US008895771B2

(12) United States Patent
Abraham et al.

(10) Patent No.: US 8,895,771 B2
(45) Date of Patent: Nov. 25, 2014

(54) METHODS OF MAKING ORGANIC COMPOUNDS BY METATHESIS AND HYDROCYANATION

(75) Inventors: Timothy W. Abraham, Minnetonka, MN (US); Hiroki Kaido, Eden Prairie, MN (US); Choon Woo Lee, La Canada, CA (US); Richard L. Pederson, San Gabriel, CA (US); Yann Schrodi, Agoura Hills, CA (US); Michael John Tupy, Crystal, MN (US); Alexandre A. Pletnev, Etna, NH (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 898 days.

(21) Appl. No.: 12/422,109

(22) Filed: Apr. 10, 2009

(65) Prior Publication Data
US 2009/0259065 A1 Oct. 15, 2009

Related U.S. Application Data

(63) Continuation-in-part of application No. PCT/US2007/021931, filed on Oct. 15, 2007.

(60) Provisional application No. 60/851,367, filed on Oct. 13, 2006.

(51) Int. Cl.
*C07C 253/10* (2006.01)
*B01J 31/22* (2006.01)
*C07C 6/04* (2006.01)
*C11C 3/04* (2006.01)
*C07C 45/44* (2006.01)
*C07C 227/10* (2006.01)
*C07C 51/08* (2006.01)
*C07C 51/353* (2006.01)
*C07C 67/333* (2006.01)

(52) U.S. Cl.
CPC ........... *C07C 51/353* (2013.01); *B01J 31/2265* (2013.01); *C07C 6/04* (2013.01); *C11C 3/04* (2013.01); *B01J 2531/821* (2013.01); *C07C 253/10* (2013.01); *B01J 31/2278* (2013.01); *C07C 45/44* (2013.01); *C07C 227/10* (2013.01); *B01J 2231/54* (2013.01); *C07C 51/08* (2013.01); *C07C 2531/24* (2013.01); *C07C 67/333* (2013.01)
USPC .......................................................... 558/340

(58) Field of Classification Search
USPC ....................................................... 558/340
See application file for complete search history.

(56) References Cited

U.S. PATENT DOCUMENTS

| 5,142,072 A | 8/1992 | Stipp et al. |
| 5,312,940 A | 5/1994 | Grubbs et al. |
| 5,710,298 A | 1/1998 | Grubbs et al. |
| 5,728,785 A | 3/1998 | Grubbs et al. |
| 5,728,917 A | 3/1998 | Grubbs et al. |
| 5,750,815 A | 5/1998 | Grubbs et al. |
| 5,811,515 A | 9/1998 | Grubbs et al. |
| 5,831,108 A | 11/1998 | Grubbs et al. |
| 5,849,851 A | 12/1998 | Grubbs et al. |
| 5,880,231 A | 3/1999 | Grubbs et al. |
| 5,917,071 A | 6/1999 | Grubbs et al. |
| 5,922,863 A | 7/1999 | Grubbs et al. |
| 5,939,504 A | 8/1999 | Woodson, Jr. et al. |
| 5,969,170 A | 10/1999 | Grubbs et al. |
| 5,977,393 A | 11/1999 | Grubbs et al. |
| 6,020,443 A | 2/2000 | Woodson, Jr. et al. |
| 6,040,363 A | 3/2000 | Warner et al. |
| 6,080,826 A | 6/2000 | Grubbs et al. |
| 6,107,420 A | 8/2000 | Grubbs et al. |
| 6,169,198 B1 | 1/2001 | Fischer et al. |
| 6,197,894 B1 | 3/2001 | Sunaga et al. |
| 6,211,315 B1 | 4/2001 | Larock et al. |
| 6,215,019 B1 | 4/2001 | Pederson et al. |
| 6,284,852 B1 | 9/2001 | Lynn et al. |
| 6,306,988 B1 | 10/2001 | Grubbs et al. |
| 6,310,121 B1 | 10/2001 | Woodson, Jr. et al. |
| 6,316,380 B1 | 11/2001 | Nolan et al. |
| 6,323,296 B1 | 11/2001 | Warner et al. |
| 6,376,690 B1 | 4/2002 | Grubbs et al. |
| 6,409,875 B1 | 6/2002 | Giardello et al. |
| 6,410,110 B1 | 6/2002 | Warner et al. |
| 6,410,666 B1 | 6/2002 | Grubbs et al. |
| 6,426,419 B1 | 7/2002 | Grubbs et al. |
| 6,433,101 B1 | 8/2002 | Woodson, Jr. et al. |
| 6,465,590 B1 | 10/2002 | Maughon et al. |

(Continued)

FOREIGN PATENT DOCUMENTS

EP 0429995 A2 6/1991
EP 1408064 A1 4/2004

(Continued)

OTHER PUBLICATIONS

Chatterjee et al. "Synthesis of Trisubstituted Alkenes via Olefin Cross-Metathesis" Organic Letters, 1999, vol. 1, pp. 1751-1753.*
McMurry "Organic Chemistry, Fourth Edition" Brooks/Cole Publishing Company, 1996, pp. 834-837.*
Patel et al. "Cross-metathesis of unsaturated natural oils with 2-butene. High conversion and productive catalyst turnovers" Chem. Commun, 2005, pp. 5546-5547.*

(Continued)

*Primary Examiner* — Joseph Kosack
(74) *Attorney, Agent, or Firm* — Brinks Gilson & Lione

(57) ABSTRACT

The invention is directed to methods of making organic compounds by metathesis and hydrocyanation. The method of the invention may be used, for example, to make industrial important organic compounds such as diacids, diesters, acid-amines, acid-alcohols, acid-nitriles, ester-amines, ester-alcohols, and ester-nitriles.

9 Claims, No Drawings

(56) References Cited

U.S. PATENT DOCUMENTS

| | | | |
|---|---|---|---|
| 6,486,264 | B1 | 11/2002 | Tsunogae et al. |
| 6,525,125 | B1 | 2/2003 | Giardello et al. |
| 6,583,236 | B1 | 6/2003 | Giardello et al. |
| 6,610,626 | B2 | 8/2003 | Grubbs et al. |
| 6,613,910 | B2 | 9/2003 | Grubbs et al. |
| 6,620,955 | B1 | 9/2003 | Pederson et al. |
| 6,696,597 | B2 | 2/2004 | Pedersen et al. |
| 6,759,537 | B2 | 7/2004 | Grubbs et al. |
| 6,794,534 | B2 | 9/2004 | Grubbs et al. |
| 6,803,429 | B2 | 10/2004 | Morgan et al. |
| 6,818,586 | B2 | 11/2004 | Grubbs et al. |
| 6,838,489 | B2 | 1/2005 | Bell et al. |
| 6,884,859 | B2 | 4/2005 | Grubbs et al. |
| 6,900,347 | B2 | 5/2005 | Paulson et al. |
| 6,921,735 | B2 | 7/2005 | Hoveyda et al. |
| 6,921,736 | B1 | 7/2005 | Nolan et al. |
| 6,946,533 | B2 | 9/2005 | Grubbs et al. |
| 6,962,729 | B2 | 11/2005 | Tokas et al. |
| 6,987,154 | B2 | 1/2006 | Choi et al. |
| 7,026,495 | B1 | 4/2006 | Pedersen et al. |
| 7,034,096 | B2 | 4/2006 | Choi et al. |
| 7,109,348 | B1 | 9/2006 | Nolan |
| 7,119,216 | B2 | 10/2006 | Newman et al. |
| 7,176,336 | B2 | 2/2007 | Maughon et al. |
| 7,205,424 | B2 | 4/2007 | Nolan |
| 7,285,593 | B1 | 10/2007 | Giardello et al. |
| 7,314,904 | B2 | 1/2008 | Nadolsky et al. |
| 7,329,758 | B1 | 2/2008 | Grubbs et al. |
| 7,365,140 | B2 | 4/2008 | Piers et al. |
| 7,507,854 | B2 | 3/2009 | Lee et al. |
| 7,576,227 | B2 | 8/2009 | Lysenko |
| 7,585,990 | B2 | 9/2009 | van Toor et al. |
| 7,598,330 | B2 | 10/2009 | Grubbs et al. |
| 7,622,590 | B1 | 11/2009 | Nolan et al. |
| 7,678,932 | B2 | 3/2010 | Thurier et al. |
| 7,812,185 | B2 | 10/2010 | Burdett et al. |
| 2002/0095007 | A1 | 7/2002 | Larock et al. |
| 2003/0055262 | A1 | 3/2003 | Grubbs et al. |
| 2003/0100776 | A1 | 5/2003 | Grubbs et al. |
| 2003/0186035 | A1 | 10/2003 | Cruce et al. |
| 2003/0236377 | A1 | 12/2003 | Choi et al. |
| 2005/0027136 | A1 | 2/2005 | Toor et al. |
| 2005/0070750 | A1 | 3/2005 | Newman et al. |
| 2005/0080301 | A1* | 4/2005 | Maughon et al. ............ 568/876 |
| 2005/0154221 | A1 | 7/2005 | Lysenko et al. |
| 2005/0261451 | A1 | 11/2005 | Ung et al. |
| 2006/0079704 | A1 | 4/2006 | Lacombe et al. |
| 2006/0128912 | A1 | 6/2006 | Piers et al. |
| 2006/0289138 | A1 | 12/2006 | Borsinger et al. |
| 2007/0179307 | A1 | 8/2007 | Olivier-Bourbigou et al. |
| 2007/0270621 | A1 | 11/2007 | Millis et al. |
| 2008/0027194 | A1 | 1/2008 | Schrodi |
| 2008/0064891 | A1 | 3/2008 | Lee |
| 2009/0048459 | A1 | 2/2009 | Tupy et al. |
| 2009/0126602 | A1 | 5/2009 | Murphy et al. |
| 2009/0217568 | A1 | 9/2009 | Murphy et al. |
| 2009/0220443 | A1 | 9/2009 | Braksmayer et al. |
| 2009/0264672 | A1 | 10/2009 | Abraham et al. |
| 2010/0047499 | A1 | 2/2010 | Braksmayer et al. |
| 2010/0094034 | A1 | 4/2010 | Kaido et al. |
| 2010/0145086 | A1 | 6/2010 | Schrodi et al. |

FOREIGN PATENT DOCUMENTS

| | | | | |
|---|---|---|---|---|
| FR | | 2878246 A1 | 5/2006 | |
| JP | | 56-077243 A | 6/1981 | |
| JP | | 09-014574 A | 1/1997 | |
| SU | | 1565872 A1 | 7/1988 | |
| WO | | WO 94/23836 A1 | 10/1994 | |
| WO | | WO 96/04289 A1 | 2/1996 | |
| WO | | WO 01/36368 A2 | 5/2001 | |
| WO | | WO 03/093215 A1 | 11/2003 | |
| WO | | WO 2004/062763 A2 | 7/2004 | |
| WO | | WO 2005/026106 A1 * | 3/2005 | ............ C07C 255/19 |
| WO | | WO 2005/080455 A1 | 9/2005 | |
| WO | | WO 2006/052688 A2 | 5/2006 | |
| WO | | WO 2007/081987 A2 | 7/2007 | |
| WO | | WO 2007/103398 A1 | 9/2007 | |
| WO | | WO 2007/103460 A2 | 9/2007 | |
| WO | | WO 2008/008420 A1 | 1/2008 | |
| WO | | WO 2008/010961 A2 | 1/2008 | |
| WO | | WO 2008/046106 A2 | 4/2008 | |
| WO | | WO 2008/048520 A2 | 4/2008 | |
| WO | | WO 2008/048522 A1 | 4/2008 | |
| WO | | WO 2008/063322 A2 | 5/2008 | |
| WO | | WO 2008/140468 A2 | 11/2008 | |

OTHER PUBLICATIONS

Birdwhistell et al. "Simple Synthesis and Use of a Nickel Alkene Isomerization Catalyst" Journal of Chemical Education, 1997, vol. 74, pp. 579-581.*

International Search Report and Written Opinion of the International Searching Authority for International Application No. PCT/US2007/021931, dated Apr. 11, 2008, 7 pages.

Anderson et al., "Synthesis and Reactivity of Olefin Metathesis Catalysts Bearing Cyclic (Alkyl)(Amino) Carbenes," Angewandte Chemie International Edition, vol. 46, 2007, pp. 7262-7265.

Baumann et al., "Natural Fats and Oils—Renewable Raw Materials for the Chemical Industry," Angewandte Chemie International Edition in English, vol. 27, 1988, pp. 41-62.

Biermann et al., "New Syntheses with Oils and Fats as Renewable Raw Materials for the Chemical Industry,", Angewandte Chemie International Edition, vol. 39, 2000, pp. 2206-2224.

Boelhouwer et al., "Metathesis Reactions of Fatty Acid Esters," Progress of Lipid Research, Pergamon Press, vol. 24, No. 3, 1985, pp. 243-267.

Choi et al., "Olefin Metathesis Involving Ruthenium Enoic Carbene Complexes," Journal of the American Chemical Society, vol. 123, No. 42, 2001, pp. 10417-10418.

Connon et al., "A Solid-Supported Phosphine-Free Ruthenium Alkylidene for Olefin Metathesis in Methanol and Water," Bioorganic & Medical Chem Letters, vol. 12, No. 14, 2002, pp. 1873-1876.

Dunne et al., "A Highly Efficient Olefin Metathesis Initiator: Improved Synthesis and Reactivity Studies," Tetrahedron Letters, vol. 44, No. 13, 2003, pp. 2733-2736.

Erhan et al., "Drying Properties of Metathesized Soybean Oil," Journal of American Oil Chemists' Society, AOCS Press, vol. 74, No. 6, 1997, pp. 703-706.

Lavallo, "Stable Cyclic (Alkyl)(Amino) Carbenes as Rigid or Flexible, Bulky, Electron-Rich Ligands for Transition-Metal Catalysts: A Quaternary Carbon Atom Makes the Difference," Angewandte Chemie Int. Ed., vol. 44, 2005, pp. 5705-5709.

Maynard et al., "Purification Technique for the Removal of Ruthenium from Olefin Metathesis Reaction Products," Tetrahedron Letters, vol. 40, No. 22, 1999, pp. 4137-4140.

Mol, "Applications of Olefin Metathesis in Oleochemistry: An Example of Green Chemistry," Green Chemistry, Royal Society of Chemistry, Cambridge, GB, vol. 4, 2002, pp. 5-13.

Mol et al., "Metathesis in Oleochemistry," J Braz Chem Soc, vol. 9, No. 1, 1998, pp. 1-11.

Mol, "Catalytic Metathesis of Unsaturated Fatty Acid Esters and Oils," Topics in Catalysis, vol. 27, No. 1-4, 2004, pp. 97-104.

Patel et al., "High conversion and productive catalyst turnovers in cross-metathesis reactions of natural oils with 2-butene", Green Chemistry, 2006, vol. 8, pp. 450-454.

Refvik et al., "Ruthenium-Catalyzed Metathesis of Vegetable Oils," Journal of American Oil Chemists' Society, AOCS Press, vol. 76, No. 1, 1999, pp. 93-98.

Schneider et al., "Synthesis of Highly Substituted Cyclopentane and Tetrahydrofuran Derivatives by Crossed Olefin Metathesis," Angewandte Chemi International Edition, vol. 35, No. 4, 1996, pp. 411-412.

Tian et al., "Model Studies and the ADMET Polymerization of Soybean Oil," Journal of American Oil Chemists' Society, AOCS Press, vol. 79, No. 5, 2002, pp. 479-488.

(56) References Cited

OTHER PUBLICATIONS

Delaude et al., Metathesis, Kirk-Othmer Encyclopedia of Chemical Technology, Dec. 2005, vol. 26, pp. 920-958.
Ngo et al., Methathesis of Unsaturated Fatty Acids: Synthesis of Long-Chain Unsaturated-[alpha],[omega]-Dicarboxylic Acids, Journal of the American Oil Chemists, Jul. 2006, vol. 83m Iss, 7, p. 629, 9 pgs.
Refvik, M.D. et al., "The Chemistry of Metathesized Soybean Oil," JAOCS, vol. 76, No. 1, 1999, pp. 99-102.
Verkuijlen et al., "Metathesis of Unsaturated Fatty Esters", Fette, Seifen, Anstrichmittel, Industrieverlag Von Hernhaussen KG., Hamburg, DE, vol. 78, No. 11, Jan. 1, 1976, pp. 444-447.
Communication issued in European Patent Application No. 07874079.2, dated Jul. 22, 2014, 7 pages.

* cited by examiner

METHODS OF MAKING ORGANIC COMPOUNDS BY METATHESIS AND HYDROCYANATION

CROSS-REFERENCE TO RELATED APPLICATIONS

This application is a continuation-in-part of International Application No. PCT/US2007/021931, filed Oct. 15, 2007, which claims the benefit of U.S. Provisional Application having Ser. No. 60/851,367, filed Oct. 13, 2006, and entitled METHODS OF MAKING ORGANIC COMPOUNDS BY METATHESIS AND CATALYTIC MODIFICATION, the disclosures of which are incorporated herein by reference.

BACKGROUND

It is desirable to use renewable feedstocks (e.g., natural oil-derived fatty acids or fatty esters) as a source material for synthesizing industrially important organic compounds that have been conventionally manufactured from petroleum feedstocks. One useful reaction for modifying the structure of natural oil-derived feedstocks is metathesis. Metathesis is a catalytic reaction involving the rupture and reformation of carbon-carbon double bonds. When metathesis is applied directly to many natural oil-derived feedstocks, a mixture of products results. For example, when metathesis is applied to a mixture of fatty acid esters, the resulting metathesis products include a mixture of monoesters and diesters of various chain lengths. Due to the similarity in molecular weight and functionality of the products, it is difficult to separate the desired product (e.g., a particular chain length diester) from the other metathesis products. In view of the foregoing, what is desired is a method by which organic compounds may be readily synthesized from natural oil-derived feedstock materials.

SUMMARY

The invention is directed to methods of making organic compounds by metathesis and hydrocyanation. Hydrocyanation functions to introduce a nitrile group into the organic compound. The nitrile group may be converted into an amine group, an aldehyde group, an alcohol group, or a carboxylic acid group. The methods of the invention may be used to make industrial important organic compounds, for example, dicarboxylic acids (diacids), diesters, acid-amines, acid-alcohols, acid-nitriles, ester-amines, ester-alcohols, ester-nitriles, and acid-esters.

Advantageously, the method of the invention makes use of a cross-metathesis step with a short-chain olefin to chemically modify the starting composition and to produce a functionalized alkene intermediate that has a pre-determined carbon-carbon double bond position. Upon separation of the functionalized alkene intermediate, the carbon-carbon double bond is modified by hydrocyanation in order to introduce a nitrile group into the molecule. The cross-metathesis step allows the use of starting compositions that contain multiple unsaturated species (e.g., including polyunsaturated species) to produce desired organic acid compounds. Accordingly, starting compositions comprising multiple unsaturated species may be used directly in the method without prior purification.

In one aspect, the invention provides a method of making organic compounds by metathesis and catalytic modification. The method of the invention comprises the steps of:

(a) providing a starting composition comprising an unsaturated fatty acid, an unsaturated fatty ester, a salt of unsaturated fatty acid, or a mixture thereof;
(b) cross-metathesizing the starting composition of step (a) with a short-chain olefin in the presence of a metathesis catalyst to form cross-metathesis products comprising:
 (i) one or more olefin compounds; and
 (ii) an acid-, ester-, or salt-functionalized alkene having at least one carbon-carbon double bond;
(c) separating at least a portion of the acid-, ester-, or salt-functionalized alkene from the cross-metathesis products; and
(d) catalytically modifying the carbon-carbon double bond of the acid-, ester-, or salt-functionalized alkene by hydrocyanation in order to introduce a nitrile group.

Useful starting compositions include unsaturated compounds (e.g., unsaturated fatty acids, unsaturated fatty esters, and carboxylate salts of unsaturated fatty acids) that are typically derived from natural oils such as vegetable oils or animal fats. In many embodiments, the starting composition comprises an unsaturated polyol ester.

When derived from a vegetable oil, useful vegetable oils include soybean oil, rapeseed oil, corn oil, sesame oil, cottonseed oil, sunflower oil, canola oil, safflower oil, palm oil, palm kernel oil, linseed oil, castor oil, olive oil, peanut oil, and mixtures thereof.

In the methods of the invention the starting composition is cross-metathesized with a short-chain olefin in the presence of a metathesis catalyst. In some embodiments, the short-chain olefin has the structure:

$$R^7R^8C{=}CR^9R^{10}$$

where $R^7$, $R^8$, $R^9$, and $R^{10}$ are each, independently, hydrogen or an organic group, with the proviso that at least one of $R^7$ or $R^8$ is an organic group. In many embodiments, the short-chain olefin is a short-chain internal olefin. For example, the short-chain internal olefin may have the structure:

$$R^7R^8C{=}CR^9R^{10}$$

where $R^7$, $R^8$, $R^9$, and $R^{10}$ are each, independently, hydrogen or an organic group, with the proviso that at least one of $R^7$ or $R^8$ is an organic group, and at least one of $R^9$ or $R^{10}$ is an organic group. Useful short-chain internal olefins may be symmetric or asymmetric. When symmetric, the short-chain internal olefin may have the structure:

$$R^7CH{=}CHR^9$$

where $R^7$ and $R^9$ are the same organic group. Examples of symmetric short-chain internal olefins include 2-butene, 3-hexene, and 4-octene. Examples of asymmetric short-chain internal olefin include 2-pentene, 2-hexene, 2-heptene, 3-heptene, 2-octene, 3-octene, 2-nonene, 3-nonene, and 4-nonene. In some embodiments, the short-chain olefin is an α-olefin having the structure:

$$CH_2{=}CH{-}R^{10}$$

where $-R^{10}$ is an organic group. Examples of α-olefin include 1-propene, 1-butene, 1-pentene, 1-hexene, 1-heptene, 1-octene, and 1-nonene.

After cross-metathesis, at least a portion of the acid-, ester-, or salt-functionalized alkene is separated from the other cross-metathesis products. Useful separation processes include distillation, reactive distillation, chromatography, fractional crystallization, membrane separation, liquid/liquid extraction, or a combination thereof.

After separation, the carbon-carbon double bond of the separated acid-, ester, or salt-functionalized alkene is catalytically modified by hydrocyanation in order to introduce a nitrile group. After introduction of the nitrile group, the nitrile may be further reacted in order to modify the functionality of the compound. For example, in some embodiments, the nitrile group is reduced in order to convert the nitrile group into an aldehyde group or an alcohol group. In other embodiments, the nitrile group is subjected to hydrolysis in order to convert the nitrile group into a carboxylic acid. In yet other embodiments, the nitrile group is subjected to hydrogenation in order to convert the nitrile group into an amine.

In many embodiments, the organic compounds produced according to the present invention have chain lengths ranging from about 8 to 16 carbon atoms, for example, 12 carbon atoms.

DETAILED DESCRIPTION

The invention is directed to methods of making organic compounds by metathesis and hydrocyanation. The method of the invention may be used, for example, to make industrial important organic compounds such as diacids, diesters, acid-amines, acid-alcohols, acid-nitriles, ester-amines, ester-alcohols, and ester-nitriles.

Starting Composition (Step (a)):

As a starting composition, the method of the present invention uses unsaturated fatty acids, unsaturated fatty esters, salts of unsaturated fatty acids, or a mixture. As used herein the term "unsaturated fatty acid" refers to compounds that have an alkene chain with a terminal carboxylic acid group. The alkene chain may be a linear or branched and may optionally include one or more functional groups in addition to the carboxylic acid group. For example, some carboxylic acids include one or more hydroxyl groups. The alkene chain typically contains about 4 to about 30 carbon atoms, more typically about 4 to about 22 carbon atoms. In many embodiments, the alkene chain contains 18 carbon atoms (i.e., a C18 fatty acid). The unsaturated fatty acids have at least one carbon-carbon double bond in the alkene chain (i.e., a monounsaturated fatty acid), and may have more than one double bond (i.e., a polyunsaturated fatty acid) in the alkene chain. In exemplary embodiments, the unsaturated fatty acid has from 1 to 3 carbon-carbon double bonds in the alkene chain.

Also useful as starting compositions are unsaturated fatty esters. As used herein the term "unsaturated fatty ester" refers to a compounds that have an alkene chain with a terminal ester group. The alkene chain may be linear or branched and may optionally include one or more functional groups in addition to the ester group. For example, some unsaturated fatty esters include one or more hydroxyl groups in addition to the ester group. Unsaturated fatty esters include "unsaturated monoesters" and "unsaturated polyol esters". Unsaturated monoesters have an alkene chain that terminates in an ester group, for example, an alkyl ester group such as a methyl ester. The alkene chain of the unsaturated monoesters typically contains about 4 to about 30 carbon atoms, more typically about 4 to 22 carbon atoms. In exemplary embodiments, the alkene chain contains 18 carbon atoms (i.e., a C18 fatty ester). The unsaturated monoesters have at least one carbon-carbon double bond in the alkene chain and may have more than one double bond in the alkene chain. In exemplary embodiments, the unsaturated fatty ester has 1 to 3 carbon-carbon double bonds in the alkene chain.

Also useful as a starting composition are metal salts of unsaturated fatty acids (i.e., carboxylate salts of unsaturated fatty acids). The metal salts may be salts of alkali metals (e.g., a group IA metal such as Li, Na, K, Rb, and Cs); alkaline earth metals (e.g., group IIA metals such as Be, Mg, Ca, Sr, and Ba); group IIIA metals (e.g., B, Al, Ga, In, and Tl); group IVA metals (e.g., Sn and Pb), group VA metals (e.g., Sb and Bi), transition metals (e.g., Sc, Ti, V, Cr, Mn, Fe, Co, Ni, Cu, Zn, Zr, Mo, Ru, Rh, Pd, Ag and Cd), lanthanides or actinides.

In many embodiments, the unsaturated fatty acid, ester, or carboxylate salt has a straight alkene chain and can be represented by the general formula:

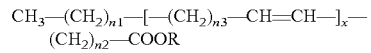

where:
R is hydrogen (fatty acid), an aliphatic group (fatty ester), or a metal ion (carboxylate salt);
n1 is an integer equal to or greater than 0 (typically 0 to 15; more typically 0, 3, or 6);
n2 is an integer equal to or greater than 0 (typically 2 to 11; more typically 3, 4, 7, 9, or 11);
n3 is an integer equal to or greater than 0 (typically 0 to 6; more typically 1); and
x is an integer equal to or greater than 1 (typically 1 to 6, more typically 1 to 3).

A summary of some unsaturated fatty acids and esters is provided in TABLE A.

TABLE A

| | Unsaturated Fatty Acids/Esters | | |
|---|---|---|---|
| Type | General Formula | Examples of fatty acids | Examples of fatty esters |
| Monounsaturated | $CH_3-(CH_2)_{n1}-[-(CH_2)_{n3}-CH=CH-]_x-(CH_2)_{n2}-COOR$<br>Where x is 1, and n1, n2, n3, and R are as described above. | Oleic Acid (x = 1, n1 = 6; n2 = 7; n3 = 1; and R is H.) | Methyl Oleate (x = 1. n1 = 6; n2 = 7; n3 = 1; and R is CH3.) |
| Polyunsaturated | Diunsaturated<br>$CH_3-(CH_2)_{n1}-[-(CH_2)_{n3}-CH=CH-]_x-(CH_2)_{n2}-COOR$<br>Where x is 2, and n1, n2, n3, and R are as described above. | Linoleic acid (x = 2, n1 = 3; n2 = 7; n3 = 1; | Methyl Linoleate (x = 2, n1 = 3; n2 = 7; n3 = 1; |

TABLE A-continued

Unsaturated Fatty Acids/Esters

| Type | General Formula | Examples of fatty acids | Examples of fatty esters |
|------|-----------------|-------------------------|--------------------------|
| | | and R is H.) | and R is CH3.) |
| Triunsaturated $CH_3—(CH_2)_{n1}—[—(CH_2)_{n3}—CH=CH—]_x—(CH_2)_{n2}—COOR$ Where x is 3, and n1, n2, n3, and R are as described above. | | Linolenic acid (x = 3, n1 = 0; n2 = 7; n3 = 1; and R is H.) | Methyl Linolenate (x = 3, n1 = 0; n2 = 7; n3 = 1; and R is CH3.) |

Unsaturated monoesters may be alkyl esters (e.g., methyl esters) or aryl esters and may be derived from unsaturated fatty acids by esterification, or unsaturated glycerides by transesterifying, with a monohydric alcohol. The monohydric alcohol may be any monohydric alcohol that is capable of reacting with the unsaturated free fatty acid or unsaturated glyceride to form the corresponding unsaturated monoester. In some embodiments, the monohydric alcohol is a C1 to C20 monohydric alcohol, for example, a C1 to C12 monohydric alcohol, a C1 to C8 monohydric alcohol, or a C1 to C4 monohydric alcohol. The carbon atoms of the monohydric alcohol may be arranged in a straight chain or in a branched chain structure, and may be substituted with one or more substituents. Representative examples of monohydric alcohols include methanol, ethanol, propanol (e.g., isopropanol), and butanol.

Transesterification of an unsaturated triglyceride can be represented as follows.

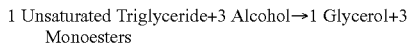

1 Unsaturated Triglyceride+3 Alcohol→1 Glycerol+3 Monoesters

Depending upon the make-up of the unsaturated triglyceride, the above reaction may yield one, two, or three moles of unsaturated monoester. Transesterification is typically conducted in the presence of a catalyst, for example, alkali catalysts, acid catalysts, or enzymes. Representative alkali transesterification catalysts include NaOH, KOH, sodium and potassium alkoxides (e.g., sodium methoxide), sodium ethoxide, sodium propoxide, sodium butoxide. Representative acid catalysts include sulfuric acid, phosphoric acid, hydrochloric acid, and sulfonic acids. Heterogeneous catalysts may also be used for transesterification. These include alkaline earth metals or their salts such as CaO, MgO, calcium acetate, barium acetate, natural clays, zeolites, Sn, Ge or Pb, supported on various materials such as ZnO, MgO, $TiO_2$, activated carbon or graphite, and inorganic oxides such as alumina, silica-alumina, boria, oxides of P, Ti, Zr, Cr, Zn, Mg, Ca, and Fe. In exemplary embodiments, the triglyceride is transesterified with methanol ($CH_3OH$) in order to form free fatty acid methyl esters.

In some embodiments, the unsaturated fatty esters are unsaturated polyol esters. As used herein the term "unsaturated polyol ester" refers to compounds that have at least one unsaturated fatty acid that is esterified to the hydroxyl group of a polyol. The other hydroxyl groups of the polyol may be unreacted, may be esterified with a saturated fatty acid, or may be esterified with an unsaturated fatty acid. The fatty acids in the polyol ester may be linear or branched and may optionally have functional groups other than the carboxylic acid such as one or more hydroxyl groups. Examples of polyol include glycerol, 1,3-propanediol, 1,2-propenediol, ethylene glycol, 1,4-butanediol, 2,3-butanediol, 1,6-hexanediol, 1,5-pentanediol, trimethylolpropane, erythritol, pentaerythritol, and sorbitol. In many embodiments, unsaturated polyol esters have the general formula:

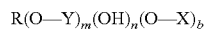

$$R(O—Y)_m(OH)_n(O—X)_b$$

where
R is an organic group having a valency of (n+m+b);
m is an integer from 0 to (n+m+b−1), typically 0 to 2;
b is an integer from 1 to (n+m+b), typically 1 to 3;
n is an integer from 0 to (n+m+b—1), typically 0 to 2;
(n+m+b) is an integer that is 2 or greater;
X is —(O)C—$(CH_2)_{n2}$—[—CH=CH—$(CH_2)_{n3}$—]$_x$—$(CH_2)_{n1}$—$CH_3$;
Y is —(O)C—R';
R' is a straight or branched chain alkyl or alkenyl group;
n1 is an integer equal to or greater than 0 (typically 0 to 15; more typically 0, 3, or 6);
n2 is an integer equal to or greater than 0 (typically 2 to 11; more typically 3, 4, 7, 9, or 11);
n3 is an integer equal to or greater than 0 (typically 0 to 6; more typically 1); and
x is an integer equal to or greater than 1 (typically 1 to 6, more typically 1 to 3).

In many embodiments, the unsaturated polyol esters are unsaturated glycerides. As used herein the term "unsaturated glyceride" refers to a polyol ester having at least one (e.g., 1 to 3) unsaturated fatty acid that is esterified with a molecule of glycerol. The fatty acid groups may be linear or branched and may include pendant hydroxyl groups. In many embodiments, the unsaturated glycerides are represented by the general formula:

$CH_2A$-$CHB$—$CH_2C$ where -A; —B; and —C are selected from
—OH;
—O(O)C—$(CH_2)_{n2}$—[—CH=CH—$(CH_2)_{n3}$—]$_x$—$(CH_2)_{n1}$—$CH_3$; and
—O(O)C—R';
with the proviso that at least one of -A, —B, or —C is
—O(O)C—$(CH_2)_{n2}$—[—CH=CH—$(CH_2)_{n3}$—]$_x$—$(CH_2)_{n1}$—$CH_3$.
In the above formula:
R' is a straight or branched chain alkyl or alkenyl group;
n1 is an integer equal to or greater than 0 (typically 0 to 15; more typically 0, 3, or 6);
n2 is an integer equal to or greater than 0 (typically 2 to 11; more typically 3, 4, 7, 9, or 11);

n3 is an integer equal to or greater than 0 (typically 0 to 6; more typically 1); and x is an integer equal to or greater than 1 (typically 1 to 6, more typically 1 to 3).

Unsaturated glycerides having two —OH groups (e.g., -A and —B are —OH) are commonly known as unsaturated monoglycerides. Unsaturated glycerides having one —OH group are commonly known as unsaturated diglycerides. Unsaturated glycerides having no —OH groups are commonly known as unsaturated triglycerides.

As shown in the formula above, the unsaturated glyceride may include monounsaturated fatty acids, polyunsaturated fatty acids, and saturated fatty acids that are esterified to the glycerol molecule. The main chain of the individual fatty acids may have the same or different chain lengths. Accordingly, the unsaturated glyceride may contain up to three different fatty acids so long as at least one fatty acid is an unsaturated fatty acid.

In many embodiments, useful starting compositions are derived from natural oils, such as plant-based oils, animal fats, or algae oils. Representative examples of plant-based oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, castor oil, tall oil, and the like. Representative examples of animal fats include lard, tallow, chicken fat (yellow grease), and fish oil.

In many embodiments, the plant-based oil is soybean oil. Soybean oil comprises unsaturated glycerides, for example, in many embodiments about 95% weight or greater (e.g., 99% weight or greater) triglycerides. Major fatty acids making up soybean oil include saturated fatty acids, for example, palmitic acid (hexadecanoic acid) and stearic acid (octadecanoic acid), and unsaturated fatty acids, for example, oleic acid (9-octadecenoic acid), linoleic acid (9,12-octadecadienoic acid), and linolenic acid (9,12,15-octadecatrienoic acid). Soybean oil is a highly unsaturated vegetable oil with many of the triglyceride molecules having at least two unsaturated fatty acids.

The method of the invention can be used to produce multiple organic acid compounds. As discussed below, the position of the carbon-carbon double bond closest to the carboxylic acid, ester, or carboxylate salt group dictates the chain length of the organic acid compound that is formed by the method of the invention.

Δ9 Starting Compositions:

In many embodiments, the starting composition comprises a Δ9 unsaturated fatty acid, a Δ9 unsaturated fatty ester (e.g., monoesters or polyol esters), a Δ9 unsaturated fatty acid salt, or a mixture of two or more of the foregoing. Δ9 unsaturated starting materials have a carbon-carbon double bond located between the $9^{th}$ and $10^{th}$ carbon atoms (i.e., between C9 and C10) in the alkene chain of the unsaturated fatty acid, ester, or salt. In determining this position, the alkene chain is numbered beginning with the carbon atom in the carbonyl group of the unsaturated fatty acid, ester, or salt. Δ9 unsaturated fatty acids, esters, and salts include polyunsaturated fatty acids, esters, or salts (i.e., having more than one carbon-carbon double bond in the alkene chain) so long as one of the carbon-carbon double bonds is located between C9 and C10. For example, included within the definition of Δ9 unsaturated fatty acids, esters, or salts are Δ9, 12 unsaturated fatty acids, esters or salts, and Δ9, 12, 15 unsaturated fatty acids, esters or salts.

In many embodiments, the Δ9 unsaturated starting materials have a straight alkene chain and may be represented by the general structure:

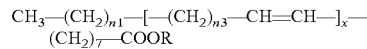

where

R is hydrogen (fatty acid), an aliphatic group (fatty monoester) or a metal ion (carboxylate salt);

n1 is an integer equal to or greater than 0 (typically 0 to 6; more typically 0, 3, 6);

n3 is an integer equal to or greater than 0 (typically 1); and x is an integer equal to or greater than 1 (typically 1 to 6, more typically 1 to 3).

In exemplary embodiments, the Δ9 unsaturated starting materials have a total of 18 carbons in the alkene chain. Examples include

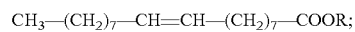

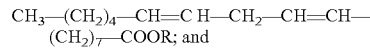

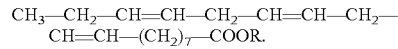

where R is hydrogen (fatty acid), an aliphatic group (fatty monoester) or a metal ion (fatty acid salt);

Δ9 unsaturated fatty esters may be monoesters or polyol esters. In many embodiments, the Δ9 unsaturated polyol esters have the general structure:

where -A; —B; and —C are independently selected from
—OH;
—O(O)C—R'; and
—O(O)C—$(CH_2)_7$—[—CH=CH—$(CH_2)_{n3}$—]$_x$—$(CH_2)_{n1}$—$CH_3$;

with the proviso that at least one of -A, —B, or —C is
—O(O)C—$(CH_2)_7$—[—CH=CH—$(CH_2)_{n3}$—]$_x$—$(CH_2)_{n1}$—$CH_3$.

In the above formula:

R' is a straight or branched chain alkyl or alkenyl group;

n1 is an integer equal to or greater than 0 (typically 0 to 6; more typically 0, 3, 6);

n3 is an integer equal to or greater than 0 (typically 1); and x is an integer equal to or greater than 1 (typically 1 to 6, more typically 1 to 3).

In exemplary embodiments, the starting composition comprises one or more C18 fatty acids, for example, oleic acid (i.e., 9-octadecenoic acid), linoleic acid (i.e., 9,12-octadecadienoic acid), and linolenic acid (i.e., 9,12,15-octadecatrienoic acid). In other exemplary embodiments, the starting composition comprises one or more C18 fatty esters, for example, methyl oleate, methyl linoleate, and methyl linolenate. In yet another exemplary embodiment, the starting composition comprises an unsaturated glyceride comprising Δ9 fatty acids, for example, C18 Δ9 fatty acids.

Δ9 starting compositions may be derived, for example, from vegetable oils such as soybean oil, rapeseed oil, corn oil, sesame oil, cottonseed oil, sunflower oil, canola oil, safflower oil, palm oil, palm kernel oil, linseed oil, castor oil, olive oil, peanut oil, and the like. Since these vegetable oils yield predominately in glyceride form, the oils are typically processed (e.g., by transesterification) to yield unsaturated fatty esters, unsaturated free fatty acids, or carboxylate salts thereof. Δ9 starting materials may also be derived from tung oil which typically contains oleic acid, linoleic acid, and elostearic acid (C18; Δ9, 11, 13) in glyceride form. Δ9 starting materials may also be derived from tall oil, fish oil, lard, and tallow.

Δ5 Starting Compositions:

Also useful as a starting composition in the methods of the present invention are Δ5 unsaturated fatty acids, esters, or salts. As used herein "Δ5" refers to unsaturated fatty acids, esters, or salts having a carbon-carbon double bond located between the 5th and 6th carbon atom in the alkene chain of the unsaturated fatty acid, ester, or salt. In some embodiments, Δ5 unsaturated fatty acids, esters, and salts have the general structure:

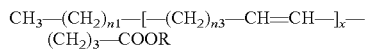

where
- R is hydrogen (fatty acid), an aliphatic group (fatty monoester) or a metal ion (carboxylate salt);
- n1 is an integer equal to or greater than 0 (typically 1 to 15; more typically 1, 13, or 15);
- n3 is an integer equal to or greater than 0 (typically 0 to 6; more typically 0 or 6); and
- x is an integer equal to or greater than 1 (typically 1 to 6, more typically 1 to 2).

The Δ5 unsaturated fatty esters may be monoesters or polyol esters (e.g., unsaturated glycerides). In many embodiments, the Δ5 unsaturated polyol esters have the general structure:

where -A; —B; and —C are independently selected from
- —OH;
- —O(O)C—R'; and
- —O(O)C—(CH$_2$)$_3$—[—CH=CH—(CH$_2$)$_{n3}$—]$_x$—(CH$_2$)$_{n1}$—CH$_3$;

with the proviso that at least one of -A, —B, or —C is
- —O(O)C—(CH$_2$)$_3$—[—CH=CH—(CH$_2$)$_{n3}$—]$_x$—(CH$_2$)$_{n1}$CH$_3$.

In the above formula:
- R' is a straight or branched chain alkyl or alkenyl group;
- n1 is an integer equal to or greater than 0 (typically 1 to 15; more typically 1, 13, or 15);
- n3 is an integer equal to or greater than 0 (typically 0 to 6; more typically 0 or 6); and
- x is an integer equal to or greater than 1 (typically 1 to 6, more typically 1 to 2).

Δ5 starting compositions may be derived, for example, from meadowfoam oil which contains a twenty carbon monounsaturated fatty acid (C20:1; Δ5) in glyceride form. Δ5 starting compositions may also be derived from fish oil which typically contains eicosapentaenoic acid (C20:5; Δ5, 8, 11, 14, 17) in glyceride form.

Δ6 Starting Compositions:

Also useful as a starting composition in the methods of the present invention are Δ6 unsaturated fatty acids, esters, or salts. As used herein "Δ6" refers to unsaturated fatty acids, esters, or salts having a carbon-carbon double bond located between the 6th and 7th carbon atom in the alkene chain of the unsaturated fatty acid, ester, or salt. In some embodiments, Δ6 unsaturated fatty acids, esters, and salts have the general structure:

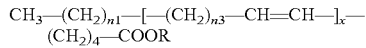

where
- R is hydrogen (fatty acid), an aliphatic group (fatty monoester) or a metal ion (carboxylate salt);
- n1 is an integer equal to or greater than 0 (typically 0 to 10);
- n3 is an integer equal to or greater than 0; (typically 0); and
- x is an integer equal to or greater than 1 (typically 1 to 6, more typically 1).

The Δ6 unsaturated fatty esters may be monoesters or polyol esters (e.g., unsaturated glycerides). In many embodiments, the Δ6 unsaturated polyol esters have the general structure:

where -A; —B; and —C are independently selected from
- —OH;
- —O(O)C—R'; and
- —O(O)C—(CH$_2$)$_4$—[—CH=CH—(CH$_2$)$_{n3}$—]$_x$—(CH$_2$)$_{n1}$—CH$_3$;

with the proviso that at least one of -A, —B, or —C is
- —O(O)C—(CH$_2$)$_4$—[—CH=CH—(CH$_2$)$_{n3}$—]$_x$—(CH$_2$)$_{n1}$—CH$_3$.

In the above formula:
- R' is a straight or branched chain alkyl or alkenyl group;
- n1 is an integer equal to or greater than 0 (typically 0 to 10);
- n3 is an integer equal to or greater than 0; (typically 0); and
- x is an integer equal to or greater than 1 (typically 1 to 6, more typically 1).

Δ6 starting compositions may be derived from coriander oil which contains an 18 carbon unsaturated fatty acid (C18:1; Δ6) in glyceride form.

Δ11 Starting Compositions:

Also useful as a starting composition in the methods of the present invention are Δ11 unsaturated fatty acids, esters, or salts. As used herein "Δ11" refers to unsaturated fatty acids, esters, or salts having a carbon-carbon double bond located between the 11$^{th}$ and 12$^{th}$ carbon atom in the alkene chain of the unsaturated fatty acid, ester, or salt. In some embodiments, Δ11 unsaturated fatty acids, esters, and salts have the general structure:

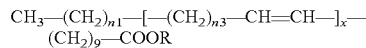

where
- R is hydrogen (fatty acid), an aliphatic group (fatty monoester) or a metal ion (carboxylate salt);
- n1 is an integer equal to or greater than 0 (typically 0 to 7; more typically 7);
- n3 is an integer equal to or greater than 0 (typically 0); and
- x is an integer equal to or greater than 1 (typically 1 to 6, more typically 1).

The Δ11 unsaturated fatty esters may be monoesters or polyol esters (e.g., unsaturated glycerides). In many embodiments, the Δ11 unsaturated polyol esters have the general structure:

where -A; —B; and —C are independently selected from
- —OH;
- —O(O)C—R'; and
- —O(O)C—(CH$_2$)$_9$—[—CH=CH—(CH$_2$)$_{n3}$—]$_x$—(CH$_2$)$_{n1}$CH$_3$;

with the proviso that at least one of -A, —B, or —C is
- —O(O)C—(CH$_2$)$_9$—[—CH=CH—(CH$_2$)$_{n3}$—]$_x$—(CH$_2$)$_{n1}$CH$_3$.

In the above formula:
- R' is a straight or branched chain alkyl or alkenyl group;
- n1 is an integer equal to or greater than 0 (typically 0 to 7; more typically 7);
- n3 is an integer equal to or greater than 0 (typically 0); and x is an integer equal to or greater than 1 (typically 1 to 6, more typically 1).

Sources of Δ11 starting compositions include camelina oil which contains gondoic acid (C20:1 Δ11) at approximately 15% of the fatty acid composition.

Δ13 Starting Compositions:

Also useful as a starting composition in the methods of the present invention are Δ13 unsaturated fatty acids, esters, or salts. As used herein "Δ13" refers to unsaturated fatty acids, esters, or salts having a carbon-carbon double bond located between the 13$^{th}$ and 14$^{th}$ carbon atom in the alkene chain of the unsaturated fatty acid, ester, or salt. In some embodiments, Δ13 unsaturated fatty acids, esters, and salts have the general structure:

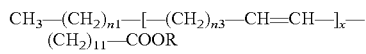

where

R is hydrogen (fatty acid), an aliphatic group (fatty monoester) or a metal ion (carboxylate salt);

n1 is an integer equal to or greater than 0 (typically 7);

n3 is an integer equal to or greater than 0 (typically 0)

x is an integer equal to or greater than 1 (typically 1 to 6, more typically 1).

The Δ13 unsaturated fatty esters may be monoesters or polyol esters (e.g., unsaturated glycerides). In many embodiments, the Δ13 unsaturated polyol esters have the general structure

where -A; —B; and —C are independently selected from
—OH;
—O(O)C—R'; and
—O(O)C—(CH$_2$)$_{11}$—[—CH=CH—(CH$_2$)$_{n3}$—]$_x$—(CH$_2$)$_{n1}$—CH$_3$, with the proviso that at least one of -A, —B, or —C is
—O(O)C—(CH$_2$)$_{11}$—[—CH=CH—(CH$_2$)$_{n3}$—]$_x$—(CH$_2$)$_{n1}$—CH$_3$.

In the above formula:

R' is a straight or branched chain alkyl or alkenyl group;

n1 is an integer equal to or greater than 0 (typically 7);

n3 is an integer equal to or greater than 0 (typically 0)

x is an integer equal to or greater than 1 (typically 1 to 6, more typically 1).

Sources of Δ13 starting compositions include crambe oil, fish oil, and high erucic acid rapeseed oil which are high in erucic acid (C22:1 Δ13) in glyceride form.

Other useful starting compositions include, for example, Δ8 and Δ4 starting materials. Δ4 starting materials may be obtained, for example, from fish oil which typically includes an amount of docosahexaenoic acid (C22:6; Δ4, 7, 10, 13, 16, 19). Δ8 starting materials may also be obtained from fish oil which typically includes an amount of eicosatetraenoic acid (C20:4; Δ8, 11, 14, 17).

A summary of some useful starting compositions is provided in TABLE B.

TABLE B

| Starting Composition | Description | Classification | Bond Locations |
|---|---|---|---|
| Oleic acid | C18 monounsaturated fatty acid (C18:1) | Δ9 | Δ9 |
| Linoleic acid | C18 diunsaturated fatty acid (C18:2) | Δ9 | Δ9, 12 |
| Linolenic acid | C18 triunsaturated fatty acid (C18:3) | Δ9 | Δ9, 12, 15 |

TABLE B-continued

| Starting Composition | Description | Classification | Bond Locations |
|---|---|---|---|
| Alkyl oleate | C18 monounsaturated fatty ester (C18:1) | Δ9 | Δ9 |
| Alkyl linoleate | C18 diunsaturated fatty ester (C18:2) | Δ9 | Δ9, 12 |
| Alkyl linolenate | C18 triunsaturated fatty ester (C18:3) | Δ9 | Δ9, 12, 15 |
| Vegetable Oil (e.g., soybean oil) | Unsaturated glycerides of C18:1, C18:2, and C18:3 fatty acids | Δ9 | Δ9<br>Δ9, 12<br>Δ9, 12, 15 |
| Tung Oil | Unsaturated glycerides of C18:1; C18:2; and C18:3 fatty acids | Δ9 | Δ9, 11, 13<br>Δ9<br>Δ9, 12 |
| Meadowfoam Oil | Unsaturated glycerides of C20:1 fatty acids. | Δ5 | Δ5 |
| Coriander Oil | Unsaturated glycerides of C18:1 fatty acids. | Δ6 | Δ6 |
| Camelina oil | Unsaturated glycerides of C20:1 fatty acids | Δ11 | Δ11 |
| Crambe Oil or High Erucic Rapeseed Oil | Unsaturated glycerides of C22:1 fatty acids | Δ13 | Δ13 |

Cross-Metathesis (Step (b)):

In the method of the present invention, the starting composition is cross-metathesized with an alpha olefin, an internal olefin, or a mixture thereof, to form cross-metathesis products comprising: (i) one or more olefins; and (ii) one or more acid-, ester-, or salt-functionalized alkenes.

In some embodiments, the internal olefin is a short-chain olefin ("SCO"). Short-chain olefins are short-chain length organic compounds that have at least one carbon-carbon double bond. Typically, the short-chain length internal olefins have between about 4 and about 9 carbon atoms. Short-chain olefins can be represented by the structure (II):

$$R^7R^8C=CR^9R^{10} \qquad (II)$$

where $R^7$, $R^8$, $R^9$, and $R^{10}$ are each, independently, hydrogen or an organic group, with the proviso that at least one of $R^7$ or $R^8$ is an organic group.

The organic group may be an aliphatic group, an alicyclic group or an aromatic group. Organic groups may optionally include heteroatoms (e.g., O, N, or S atoms), as well as functional groups (e.g., carbonyl groups). The term aliphatic group means a saturated or unsaturated, linear or branched, hydrocarbon group. This term is used to encompass alkyl groups. The term alkyl group means a monovalent, saturated, linear, branched, or cyclic hydrocarbon group. Representative examples include of alkyl groups include methyl, ethyl, propyl (n-propyl or i-propyl) butyl (n-butyl or t-butyl), and heptyl. An alicyclic group is an aliphatic group arranged in one or more closed ring structures. The term is used to encompass saturated (i.e., cycloparaffins) or unsaturated (cycloolefins or cycloacetylenes) groups. An aromatic or aryl group is an unsaturated cyclic hydrocarbon having a conjugated ring structure. Included within aromatic or aryl groups are those possessing both an aromatic ring structure and an aliphatic or alicyclic group.

In some embodiments, the short-chain olefin is a short-chain internal olefin. Short-chain internal olefins may be represented by structure (II) where $R^7$, $R^8$, $R^9$, and $R^{10}$ are each, independently, hydrogen or an organic group, with the proviso that at least one of $R^7$ or $R^8$ is an organic group, and at least one of $R^9$ or $R^{10}$ is an organic group.

Short-chain internal olefins may be symmetric or asymmetric. Symmetric short-chain internal olefins having one carbon-carbon double bond may be represented by structure (II-A):

$$R^7CH=CHR^9 \quad (II-A)$$

where —$R^7$ and —$R^9$ are same organic group.

Representative examples of symmetric short-chain internal olefins include 2-butene, 3-hexene, and 4-octene. In some embodiments, the short-chain internal olefin is asymmetric. Representative examples of asymmetric short-chain internal olefins include 2-pentene, 2-hexene, 2-heptene, 3-heptene, 2-octene, 3-octene, 2-nonene, 3-nonene, and 4-nonene.

In many embodiments, symmetric short-chain internal olefins are preferred for cross-metathesis because the cross-metathesis products that result will include fewer products than if an asymmetric short-chain internal olefin is used for cross-metathesis. For example, as shown below, when a first double-bond containing compound (i.e., A=B) is cross-metathesized with a symmetric short-chain internal olefin (i.e., represented by C=C), two cross-metathesis products are produced. By contrast, when the same double-bond containing compound is cross-metathesisized with an asymmetric short-chain internal olefin (i.e., represented by C=D), four cross-metathesis products are produced.

Metathesis of Symmetric Short-chain Internal Olefin (C=C)

$$A=B+C=C \leftrightarrow A=C+B=C$$

Metathesis of Asymmetric Short-chain Internal Olefin (C=D):

$$A=B+C=D \leftrightarrow A=C+B=C+A=D+B=D$$

In some embodiments, the short-chain olefin is an α-olefin. Alpha olefins are included in general structure (II) when $R^7$, $R^8$, and $R^9$ are all hydrogen. Representative α-olefin are shown in general structure (II-B):

$$CH_2=CH-R^{10} \quad (II-B)$$

where —$R^{10}$ is an organic group.

Representative —$R^{10}$ groups include —$CH_3$ and —$(CH_2)_n$—$CH_3$, where n ranges from 0 to 6. Exemplary alpha olefin compounds include 1-propene, 1-butene, 1-pentene, 1-hexene, 1-heptene, 1-octene, and 1-nonene.

Metathesis Catalysts:

The metathesis reaction is conducted in the presence of a catalytically effective amount of a metathesis catalyst. The term "metathesis catalyst" includes any catalyst or catalyst system which catalyzes the metathesis reaction.

Any known or future-developed metathesis catalyst may be used, alone or in combination with one or more additional catalysts, in accordance with embodiments of the present method. Exemplary metathesis catalysts include metal carbene catalysts based upon transition metals, for example, ruthenium, molybdenum, osmium, chromium, rhenium, and tungsten. In certain embodiments, the metathesis catalyst is preferably a Group 8 transition metal complex having the structure of formula (III)

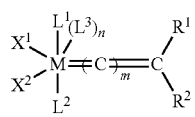

(III)

in which the various substituents are as follows:

M is a Group 8 transition metal;

$L^1$, $L^2$ and $L^3$ are neutral electron donor ligands;

n is 0 or 1, such that $L^3$ may or may not be present;

m is 0, 1, or 2;

$X^1$ and $X^2$ are anionic ligands; and $R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X^1$, $X^2$, $L^1$, $L^2$, $L^3$, $R^1$, and $R^2$ can be taken together to form a cyclic group, and further wherein any one or more of $X^1$, $X^2$, $L^1$, $L^2$, $L^3$, $R^1$, and $R^2$ may be attached to a support.

Preferred catalysts contain Ru or Os as the Group 8 transition metal, with Ru particularly preferred.

Numerous embodiments of the catalysts useful in the reactions of the disclosure are described in more detail infra. For the sake of convenience, the catalysts are described in groups, but it should be emphasized that these groups are not meant to be limiting in any way. That is, any of the catalysts useful in the disclosure may fit the description of more than one of the groups described herein.

A first group of catalysts, then, are commonly referred to as 1$^{st}$ Generation Grubbs-type catalysts, and have the structure of formula (III). For the first group of catalysts, M and m are as described above, and n, $X^1$, $X^2$, $L^1$, $L^2$, $L^3$, $R^1$, and $R^2$ are described as follows.

For the first group of catalysts, n is 0, and $L^1$ and $L^2$ are independently selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether. Exemplary ligands are trisubstituted phosphines.

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. In the most preferred embodiments, $X^1$ and $X^2$ are each chloride.

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

In preferred catalysts, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, phenyl, and a functional group Fn as defined earlier herein. Most preferably, $R^2$ is phenyl or vinyl substituted with one or more moieties selected from methyl, ethyl, chloro, bromo, iodo, fluoro, nitro, dimethylamino, methyl, methoxy, and phenyl. Optimally, $R^2$ is phenyl or —C=C(CH$_3$)$_2$.

Any two or more (typically two, three, or four) of $X^1$, $X^2$, $L^1$, $L^2$, $L^3$, $R^1$, and $R^2$ can be taken together to form a cyclic group, as disclosed, for example, in U.S. Pat. No. 5,312,940 to Grubbs et al. When any of $X^1$, $X^2$, $L^1$, $L^2$, $L^3$, $R^1$, and $R^2$ are linked to form cyclic groups, those cyclic groups may contain 4 to 12, preferably 4, 5, 6, 7 or 8 atoms, or may comprise two or three of such rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

A second group of catalysts, commonly referred to as $2^{nd}$ Generation Grubbs-type catalysts, have the structure of formula (III), wherein $L^1$ is a carbene ligand having the structure of formula (IV)

(IV)

such that the complex may have the structure of formula (V)

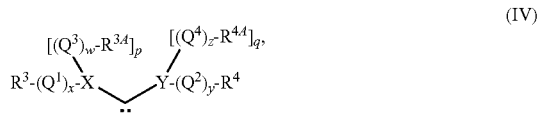

(V)

wherein M, m, n, $X^1$, $X^2$, $L^2$, $L^3$, $R^1$, and $R^2$ are as defined for the first group of catalysts, and the remaining substituents are as follows.

X and Y are heteroatoms typically selected from N, O, S, and P. Since O and S are divalent, p is necessarily zero when X is O or S, and q is necessarily zero when Y is O or S. However, when X is N or P, then p is 1, and when Y is N or P, then q is 1. In a preferred embodiment, both X and Y are N.

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. Preferably, w, x, y, and z are all zero. Further, two or more substituents on adjacent atoms within $Q^1$, $Q^2$, $Q^3$, and $Q^4$ may be linked to form an additional cyclic group.

$R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl.

In addition, any two or more of $X^1$, $X^2$, $L^1$, $L^2$, $L^3$, $R^1$, $R^2$, $R^3$, $R^{3A}$, $R^4$, and $R^{4A}$ can be taken together to form a cyclic group, and any one or more of $X^1$, $X^2$, $L^1$, $L^2$, $L^3$, $R^1$, $R^2$, $R^3$, $R^{3A}$, $R^4$, and $R^{4A}$ may be attached to a support.

Preferably, $R^{3A}$ and $R^{4A}$ are linked to form a cyclic group so that the carbene ligand is an heterocyclic carbene and preferably an N-heterocyclic carbene, such as the N-heterocylic carbene having the structure of formula (VI):

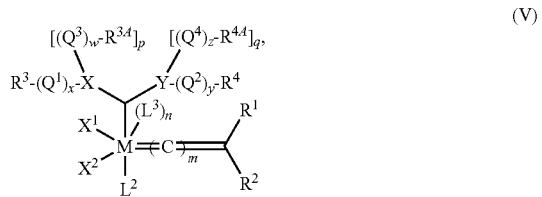

(VI)

where $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage.

Examples of N-heterocyclic carbene ligands suitable as $L^1$ thus include, but are not limited to, the following:

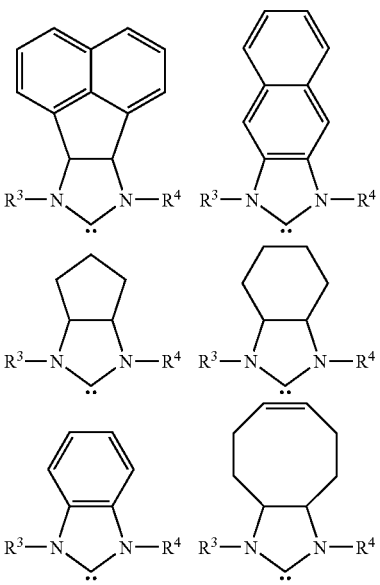

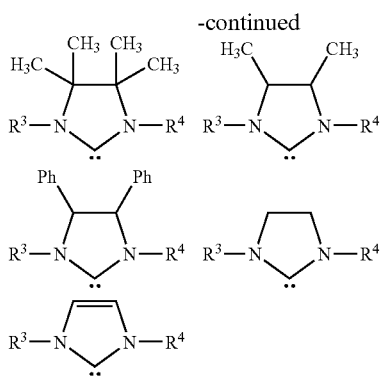

When M is ruthenium, then, the preferred complexes have the structure of formula (VII).

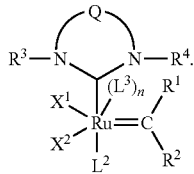

(VII)

In a more preferred embodiment, Q is a two-atom linkage having the structure $-CR^{11}R^{12}-CR^{13}R^{14}-$ or $-CR^{11}=CR^{13}-$, preferably $-CR^{11}R^{12}-CR^{13}R^{14}-$, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups. Examples of functional groups here include carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents.

When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. As an example, $R^3$ and $R^4$ are mesityl.

In a third group of catalysts having the structure of formula (III), M, m, n, $X^1$, $X^2$, $R^1$, and $R^2$ are as defined for the first group of catalysts, $L^1$ is a strongly coordinating neutral electron donor ligand such as any of those described for the first and second groups of catalysts, and $L^2$ and $L^3$ are weakly coordinating neutral electron donor ligands in the form of optionally substituted heterocyclic groups. Again, n is zero or 1, such that $L^3$ may or may not be present. Generally, in the third group of catalysts, $L^2$ and $L^3$ are optionally substituted five- or six-membered monocyclic groups containing 1 to 4, preferably 1 to 3, most preferably 1 to 2 heteroatoms, or are optionally substituted bicyclic or polycyclic structures composed of 2 to 5 such five- or six-membered monocyclic groups. If the heterocyclic group is substituted, it should not be substituted on a coordinating heteroatom, and any one cyclic moiety within a heterocyclic group will generally not be substituted with more than 3 substituents.

For the third group of catalysts, examples of $L^2$ and $L^3$ include, without limitation, heterocycles containing nitrogen, sulfur, oxygen, or a mixture thereof.

Examples of nitrogen-containing heterocycles appropriate for $L^2$ and $L^3$ include pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, and carbazole.

Examples of sulfur-containing heterocycles appropriate for $L^2$ and $L^3$ include thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thioanthrene.

Examples of oxygen-containing heterocycles appropriate for $L^2$ and $L^3$ include 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran.

Examples of mixed heterocycles appropriate for $L^2$ and $L^3$ include isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, phenoxazine, phenothiazine, pyrano[3,4-b]pyrrole, indoxazine, benzoxazole, anthranil, and morpholine.

Preferred $L^2$ and $L^3$ ligands are aromatic nitrogen-containing and oxygen-containing heterocycles, and particularly preferred $L^2$ and $L^3$ ligands are monocyclic N-heteroaryl ligands that are optionally substituted with 1 to 3, preferably 1 or 2, substituents. Specific examples of particularly preferred $L^2$ and $L^3$ ligands are pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6-dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

In general, any substituents present on $L^2$ and/or $L^3$ are selected from halo, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ alkaryl, substituted $C_6$-$C_{24}$ alkaryl, $C_6$-$C_{24}$ heteroalkaryl, substituted $C_6$-$C_{24}$ heteroalkaryl, $C_6$-$C_{24}$ aralkyl, substituted $C_6$-$C_{24}$ aralkyl, $C_6$-$C_{24}$ heteroaralkyl, substituted $C_6$-$C_{24}$ heteroaralkyl, and functional groups, with suitable functional groups including, without limitation, $C_1$-$C_{20}$ alkoxy, $C_5$-$C_{24}$ aryloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl), N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$ alkyl)-substituted amino, mono-($C_5$-$C_{24}$ aryl)-substituted amino, di-($C_5$-$C_{24}$ aryl)-substituted amino, di-N—($C_1$-$C_{20}$ alkyl), N—($C_5$-$C_{24}$ aryl)-substituted amino, $C_2$-$C_{20}$ alkylamido, $C_6$-$C_{24}$ arylamido, imino, $C_1$-$C_{20}$ alkylimino, $C_5$-$C_{24}$ arylimino, nitro, and nitroso. In addition, two adjacent substituents may be taken together to form a ring, generally a five- or six-membered alicyclic or aryl ring, optionally containing 1 to 3 heteroatoms and 1 to 3 substituents as above.

Preferred substituents on $L^2$ and $L^3$ include, without limitation, halo, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, substituted $C_6$-$C_{16}$ heteroaralkyl, $C_1$-$C_{12}$ alkoxy, $C_5$-$C_{14}$ aryloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, formyl, amino, mono-($C_1$-$C_{12}$ alkyl)-substituted amino, di-($C_1$-$C_{12}$ alkyl)-substituted amino, mono-($C_5$-$C_{14}$aryl)-substituted amino, di-($C_5$-$C_{14}$aryl)-substituted amino, and nitro.

Of the foregoing, the most preferred substituents are halo, $C_1$-$C_6$ alkyl, $C_1$-$C_6$ haloalkyl, $C_1$-$C_6$ alkoxy, phenyl, substituted phenyl, formyl, N,N-di$C_1$-$C_6$ alkyl)amino, nitro, and nitrogen heterocycles as described above (including, for example, pyrrolidine, piperidine, piperazine, pyrazine, pyrimidine, pyridine, pyridazine, etc.).

$L^2$ and $L^3$ may also be taken together to form a bidentate or multidentate ligand containing two or more, generally two, coordinating heteroatoms such as N, O, S, or P, with preferred such ligands being diimine ligands of the Brookhart type. One representative bidentate ligand has the structure of formula (VIII)

wherein $R^{15}$, $R^{16}$, $R^{17}$, and $R^{18}$ hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), heteroatom-containing hydrocarbyl (e.g., $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or substituted heteroatom-containing hydrocarbyl (e.g., substituted $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or (1) $R^{15}$ and $R^{16}$, (2) $R^{17}$ and $R^{18}$, (3) $R^{16}$ and $R^J$, or (4) both $R^{15}$ and $R^{16}$, and $R^{17}$ and $R^{18}$, may be taken together to form a ring, i.e., an N-heterocycle. Preferred cyclic groups in such a case are five- and six-membered rings, typically aromatic rings.

In a fourth group of catalysts that have the structure of formula (III), two of the substituents are taken together to form a bidentate ligand or a tridentate ligand. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$-, —As(Ph)$_2$CH$_2$CH$_2$As(Ph$_2$)-, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$—, and —OC(CH$_3$)$_2$(CH$_3$)$_2$CO—. Preferred bidentate ligands are —P(Ph)$_2$CH$_2$CH$_2$P(Ph)$_2$- and —P(CH$_3$)$_2$(CH$_2$)$_2$P(CH$_3$)$_2$—. Tridentate ligands include, but are not limited to, (CH$_3$)$_2$NCH$_2$CH$_2$P(Ph)CH$_2$CH$_2$N(CH$_3$)$_2$. Other preferred tridentate ligands are those in which any three of $X^1$, $X^2$, $L^1$, $L^2$, $L^3$, $R^1$, and $R^2$ (e.g., $X^1$, $L^1$, and $L^2$) are taken together to be cyclopentadienyl, indenyl, or fluorenyl, each optionally substituted with $C_2$-$C_{20}$ alkenyl, $C_2$-$C_{20}$ alkynyl, $C_1$-$C_{20}$ alkyl, $C_5$-$C_{20}$ aryl, $C_1$-$C_{20}$ alkoxy, $C_2$-$C_{20}$ alkenyloxy, $C_2$-$C_{20}$ alkynyloxy, $C_5$-$C_{20}$ aryloxy, $C_2$-$C_{20}$ alkoxycarbonyl, $C_1$-$C_{20}$ alkylthio, $C_1$-$C_{20}$ alkylsulfonyl, or $C_1$-$C_{20}$ alkylsulfinyl, each of which may be further substituted with $C_1$-$C_6$ alkyl, halide, $C_1$-$C_6$ alkoxy or with a phenyl group optionally substituted with halide, $C_1$-$C_6$ alkyl, or $C_1$-$C_6$ alkoxy. More preferably, in compounds of this type, X, $L^1$, and $L^2$ are taken together to be cyclopentadienyl or indenyl, each optionally substituted with vinyl, $C_1$-$C_{10}$ alkyl, $C_5$-$C_{20}$ aryl, $C_1$-$C_{10}$ carboxylate, $C_2$-$C_{10}$ alkoxycarbonyl, $C_1$-$C_{10}$ alkoxy, or $C_5$-$C_{20}$ aryloxy, each optionally substituted with $C_1$-$C_6$ alkyl, halide, $C_1$-$C_6$ alkoxy or with a phenyl group optionally substituted with halide, $C_1$-$C_6$ alkyl or $C_1$-$C_6$ alkoxy. Most preferably, X, $L^1$ and $L^2$ may be taken together to be cyclopentadienyl, optionally substituted with vinyl, hydrogen, methyl, or phenyl. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

Complexes wherein $L^2$ and $R^2$ are linked are examples of the fourth group of catalysts, and are commonly called "Grubbs-Hoveyda" catalysts. Examples of Grubbs-Hoveyda-type catalysts include the following:

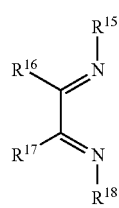

(VIII)

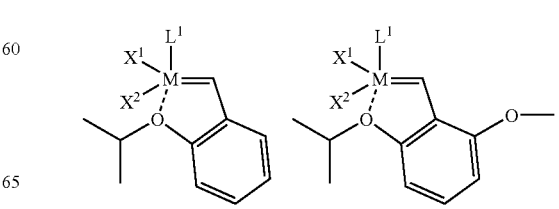

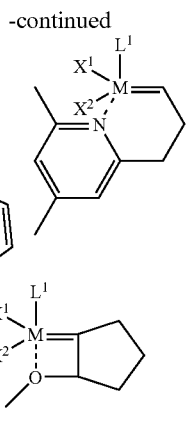

wherein $L^1$, $X^1$, $X^2$, and M are as described for any of the other groups of catalysts.

In addition to the catalysts that have the structure of formula (III), as described above, other transition metal carbene complexes include, but are not limited to:

neutral ruthenium or osmium metal carbene complexes containing metal centers that are formally in the +2 oxidation state, have an electron count of 16, are penta-coordinated, and are of the general formula (IX);

neutral ruthenium or osmium metal carbene complexes containing metal centers that are formally in the +2 oxidation state, have an electron count of 18, are hexa-coordinated, and are of the general formula (X);

cationic ruthenium or osmium metal carbene complexes containing metal centers that are formally in the +2 oxidation state, have an electron count of 14, are tetra-coordinated, and are of the general formula (XI); and cationic ruthenium or osmium metal carbene complexes containing metal centers that are formally in the +2 oxidation state, have an electron count of 14, are tetra-coordinated, and are of the general formula (XII)

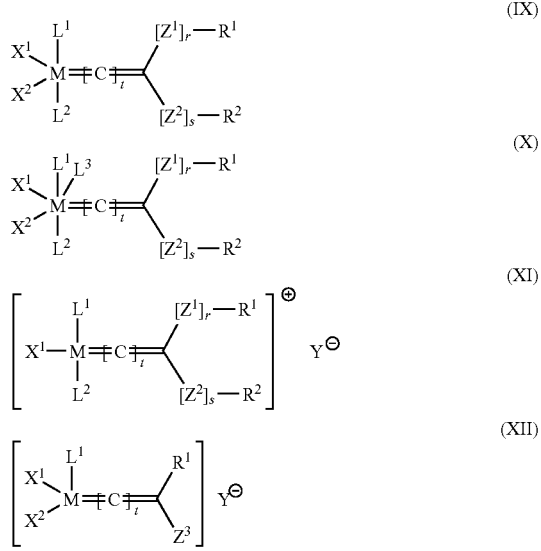

wherein: $X^1$, $X^2$, $L^1$, $L^2$, n, $L^3$, $R^1$, and $R^2$ are as defined for any of the previously defined four groups of catalysts; r and s are independently zero or 1; t is an integer in the range of zero to 5;

Y is any non-coordinating anion (e.g., a halide ion, $BF_4^-$, etc.); $Z^1$ and $Z^2$ are independently selected from —O—, —S—, —$NR^2$—, —$PR^2$—, —P(=O)$R^2$—, —P(O$R^2$)—, —P(=O)(O$R^2$)—, —C(=O)—, —C(=O)O—, —OC(=O)—, —OC(=O)O—, —S(=O)—, and —S(=O)$_2$—; $Z^3$ is any cationic moiety such as —P($R^2$)$_3^+$ or —N($R^2$)$_3^+$; and any two or more of $X^1$, $X^2$, $L^1$, $L^2$, $L^3$, n, $Z^1$, $Z^2$, $Z^3$, $R^1$, and $R^2$ may be taken together to form a cyclic group, e.g., a multidentate ligand, and wherein any one or more of $X^1$, $X^2$, $L^1$, $L^2$, n, $L^3$, $Z^1$, $Z^2$, $Z^3$, $R^1$, and $R^2$ may be attached to a support.

Other suitable complexes include Group 8 transition metal carbenes bearing a cationic substituent, such as are disclosed in U.S. Pat. No. 7,365,140 (Piers et al.) having the general structure (XIII):

wherein:
M is a Group 8 transition metal;
$L^1$ and $L^2$ are neutral electron donor ligands;
$X^1$ and $X^2$ are anionic ligands;
$R^1$ is hydrogen, $C_1$-$C_{12}$ hydrocarbyl, or substituted $C_1$-$C_{12}$ hydrocarbyl;
W is an optionally substituted and/or heteroatom-containing $C_1$-$C_{20}$ hydrocarbylene linkage;
Y is a positively charged Group 15 or Group 16 element substituted with hydrogen, $C_1$-$C_{12}$ hydrocarbyl, substituted $C_1$-$C_{12}$ hydrocarbyl; heteroatom-containing $C_1$-$C_{12}$ hydrocarbyl, or substituted heteroatom-containing hydrocarbyl;
$Z^-$ is a negatively charged counterion;
m is zero or 1; and
n is zero or 1;
wherein any two or more of $L^1$, $L^2$, $X^1$, $X^2$, $R^1$, W, and Y can be taken together to form a cyclic group.

Each of M, $L^1$, $L^2$, $X^1$, and $X^2$ in structure (XIII) may be as previously defined herein.

W is an optionally substituted and/or heteroatom-containing $C_1$-$C_{20}$ hydrocarbylene linkage, typically an optionally substituted $C_1$-$C_{12}$ alkylene linkage, e.g., —(CH$_2$)$_i$— where i is an integer in the range of 1 to 12 inclusive and any of the hydrogen atoms may be replaced with a non-hydrogen substituent as described earlier herein with regard to the definition of the term "substituted." The subscript n is zero or 1, meaning that W may or may not be present. In a preferred embodiment, n is zero.

Y is a positively charged Group 15 or Group 16 element substituted with hydrogen, $C_1$-$C_{12}$ hydrocarbyl, substituted $C_1$-$C_{12}$ hydrocarbyl, heteroatom-containing $C_1$-$C_{12}$ hydrocarbyl, or substituted heteroatom-containing hydrocarbyl. Preferably, Y is a $C_1$-$C_{12}$ hydrocarbyl-substituted, positively charged Group 15 or Group 16 element. Representative Y groups include P($R^2$)$_3$, P($R^2$)$_3$, As($R^2$)$_3$, S($R^2$)$_2$, O($R^2$)$_2$, where the $R^2$ are independently selected from $C_1$-$C_{12}$ hydrocarbyl; within these, preferred Y groups are phosphines of the structure P($R^2$)$_3$ wherein the $R^2$ are independently selected from $C_1$-$C_{12}$ alkyl and aryl, and thus include, for example, methyl, ethyl, n-propyl, isopropyl, n-butyl, isobutyl, t-butyl, cyclopentyl, cyclohexyl, and phenyl. Y can also be a heterocyclic group containing the positively charged Group 15 or Group 16 element. For instance, when the Group 15 or Group 16 element is nitrogen, Y may be an optionally substituted pyridinyl, pyrazinyl, or imidazolyl group.

$Z^-$ is a negatively charged counterion associated with the cationic complex, and may be virtually any anion, so long as the anion is inert with respect to the components of the complex and the reactants and reagents used in the metathesis reaction catalyzed. Preferred $Z^-$ moieties are weakly coordinating anions, such as, for instance, $[B(C_6F_5)_4]^-$, $[BF_4]^-$, $[B(C_6H_6)_4]^-$, $[CF_3S(O)_3]^-$, $[PF_6]^-$, $[SbF_6]^-$, $[AlCl_4]^-$, $[FSO_3]^-$, $[CB_{11}H_6Cl_6]^-$, $[CB_{11}H_6Br_6]^-$, and $[SO_3F{:}SbF_5]^-$. Preferred anions suitable as $Z^-$ are of the formula $B(R^{15})_4^-$ where $R^{15}$ is fluoro, aryl, or perfluorinated aryl, typically fluoro or perfluorinated aryl. Most preferred anions suitable as $Z^-$ are $BF_4^-$ and $B(C_6F_5)^-$, optimally the latter.

It should be emphasized that any two or more of $X^1$, $X^2$, $L^1$, $L^2$, $R^1$, W, and Y can be taken together to form a cyclic group, as disclosed, for example, in U.S. Pat. No. 5,312,940 to Grubbs et al. When any of $X^1$, $X^2$, $L^1$, $L^2$, $R^1$, W, and Y are linked to form cyclic groups, those cyclic groups may be five- or six-membered rings, or may comprise two or three five- or six-membered rings, which may be either fused or linked. The cyclic groups may be aliphatic or aromatic, and may be heteroatom-containing and/or substituted, as explained in part (I) of this section.

One group of exemplary catalysts encompassed by the structure of formula (XIII) are those wherein m and n are zero, such that the complex has the structure of formula (XIV)

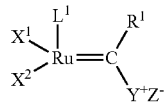

(XIV)

Possible and preferred $X^1$, $X^2$, and $L^1$ ligands are as described earlier with respect to complexes of formula (I), as are possible and preferred $Y^+$ and $Z^-$ moieties. M is Ru or Os, preferably Ru, and $R^1$ is hydrogen or $C_1$-$C_{12}$ alkyl, preferably hydrogen.

In formula (XIV)-type catalysts, $L^1$ is preferably a heteroatom-containing carbene ligand having the structure of formula (XV)

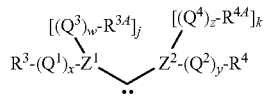

(XV)

such that complex (XIV) has the structure of formula (XVI)

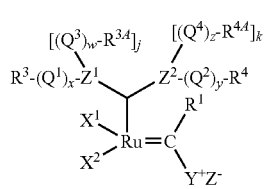

(XVI)

wherein $X^1$, $X^2$, $R^1$, $R^2$, Y, and Z are as defined previously, and the remaining substituents are as follows:

$Z^1$ and $Z^2$ are heteroatoms typically selected from N, O, S, and P. Since O and S are divalent, j is necessarily zero when $Z^1$ is O or S, and k is necessarily zero when $Z^2$ is O or S. However, when $Z^1$ is N or P, then j is 1, and when $Z^2$ is N or P, then k is 1. In a preferred embodiment, both $Z^1$ and $Z^2$ are N.

$Q^1$, $Q^2$, $Q^3$, and $Q^4$ are linkers, e.g., $C_1$-$C_{12}$ hydrocarbylene, substituted $C_1$-$C_{12}$ hydrocarbylene, heteroatom-containing $C_1$-$C_{12}$ hydrocarbylene, substituted heteroatom-containing $C_1$-$C_{12}$ hydrocarbylene, or —(CO)—, and w, x, y, and z are independently zero or 1, meaning that each linker is optional. Preferably, w, x, y, and z are all zero.

$R^3$, $R^{3A}$, $R^4$, and $R^{4A}$ are independently selected from hydrogen, hydrogen, $C_1$-$C_{20}$ hydrocarbyl, substituted $C_1$-$C_{20}$ hydrocarbyl, heteroatom-containing $C_1$-$C_{20}$ hydrocarbyl, and substituted heteroatom-containing $C_1$-$C_{20}$ hydrocarbyl.

Preferably, w, x, y, and z are zero, $Z^1$ and $Z^1$ are N, and $R^{3A}$ and $R^{4A}$ are linked to form -Q-, such that the complex has the structure of formula (XVII)

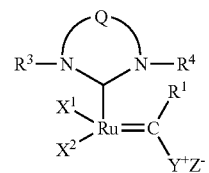

(XVII)

wherein $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including $C_1$-$C_{12}$ hydrocarbylene, substituted $C_1$-$C_{12}$ hydrocarbylene, heteroatom-containing $C_1$-$C_{12}$ hydrocarbylene, or substituted heteroatom-containing $C_1$-$C_{12}$ hydrocarbylene linker, wherein two or more substituents on adjacent atoms within Q may be linked to form an additional cyclic structure, which may be similarly substituted to provide a fused polycyclic structure of two to about five cyclic groups. Q is often, although not necessarily, a two-atom linkage or a three-atom linkage, e.g., —$CH_2$—$CH_2$—, —CH(Ph)—CH(Ph)- where Ph is phenyl; =CR—N=, giving rise to an unsubstituted (when R=H) or substituted (R=other than H) triazolyl group; or —$CH_2$—$SiR_2$—$CH_2$— (where R is H, alkyl, alkoxy, etc.).

In a more preferred embodiment, Q is a two-atom linkage having the structure —$CR^8R^9$—$CR^{10}R^{11}$— or —$CR^8$=$CR^{10}$—, preferably —$CR^8R^9$—$CR^{10}R^{11}$—, wherein $R^8$, $R^9$, $R^{10}$, and $R^{11}$ are independently selected from hydrogen, $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups as defined in part (I) of this section. Examples of functional groups here include carboxyl, $C_1$-$C_{20}$ alkoxy, $C_5$-$C_{20}$ aryloxy, $C_2$-$C_{20}$ alkoxycarbonyl, $C_2$-$C_{20}$ alkoxycarbonyl, $C_2$-$C_{20}$ acyloxy, $C_1$-$C_{20}$ alkylthio, $C_5$-$C_{20}$ arylthio, $C_1$-$C_{20}$ alkylsulfonyl, and $C_1$-$C_{20}$ alkylsulfinyl, optionally substituted with one or more moieties selected from $C_1$-$C_{10}$ alkyl, $C_1$-$C_{10}$ alkoxy, $C_5$-$C_{20}$ aryl, hydroxyl, sulfhydryl, formyl, and halide. Alternatively, any two of $R^8$, $R^9$, $R^{10}$, and $R^{11}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents.

Further details concerning such formula (XIII) complexes, as well as associated preparation methods, may be obtained from U.S. Pat. No. 7,365,140, herein incorporated by reference.

As is understood in the field of catalysis, suitable solid supports for any of the catalysts described herein may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect, if indirect, typically through a functional group on a support surface.

Non-limiting examples that may be used in the reactions of the disclosure include the following, some of which for convenience are identified throughout this disclosure by reference to their molecular weight:

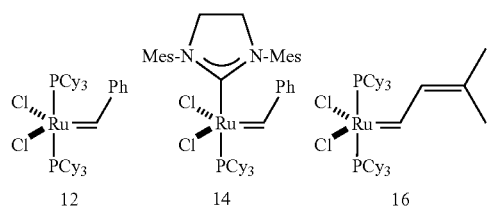

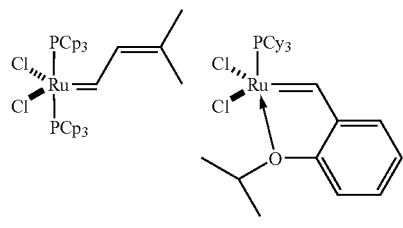

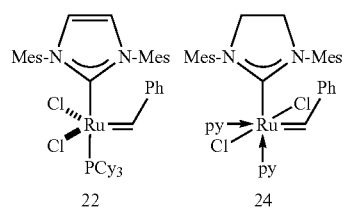

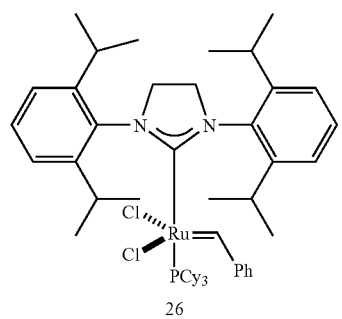

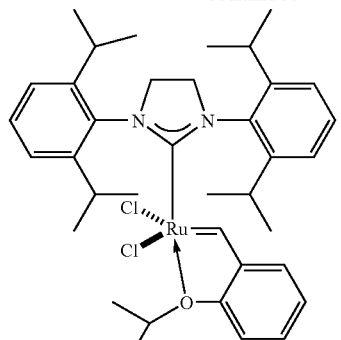

28

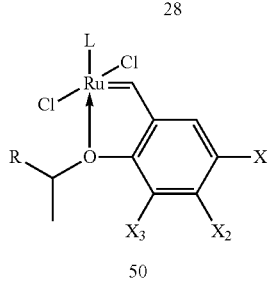

50 where
L = PCy₃, sIMes, Mes, Phobane
X = H, NO₂, SO₂N(CH₃)₂
X₂ = H, N⁺(C₂H₂)₂CH₃
X₃ = H, Phenyl
R = H, alkyl, aryl, CO₂Me

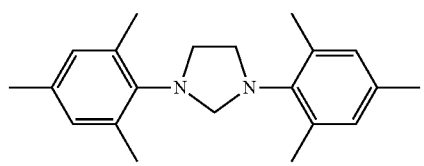

sIMes

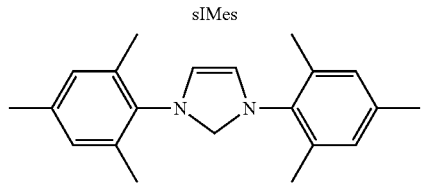

Mes

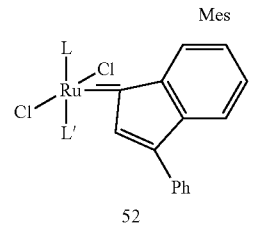

52 where
L = PCy₃, sIMes, Mes, Phobane
L' = PCy₃, Phobane

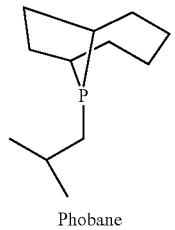

Phobane      60

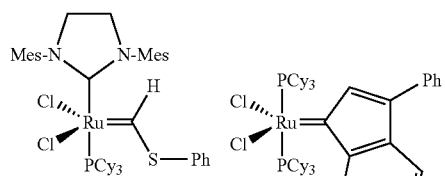
62  64
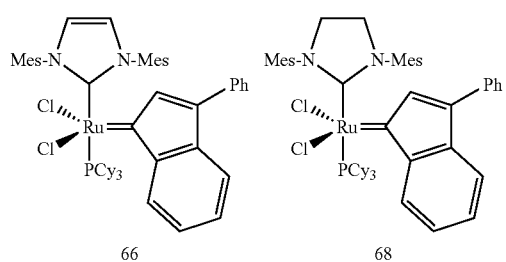
66  68
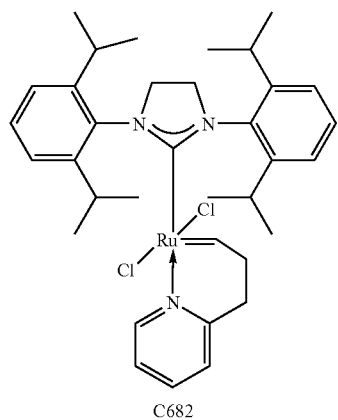
C682
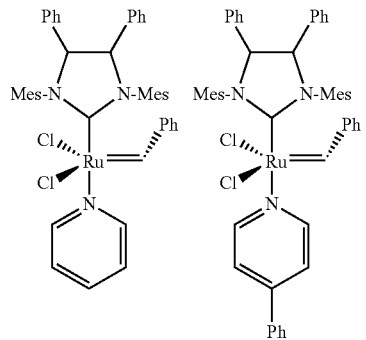
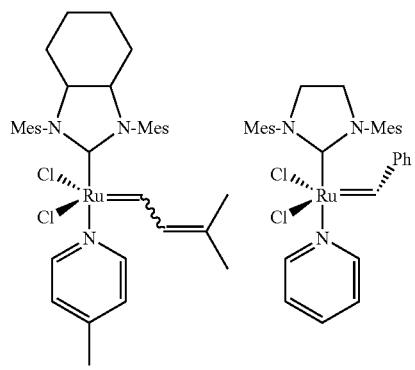
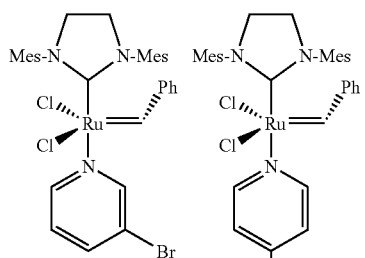
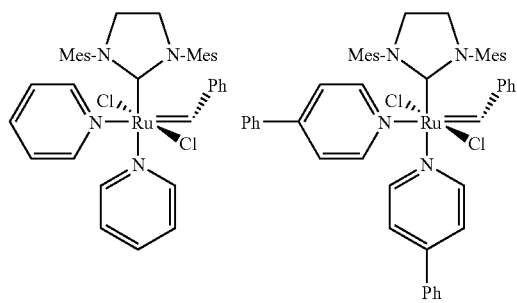
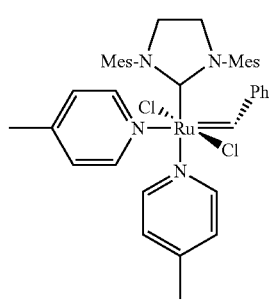
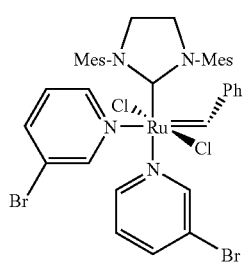
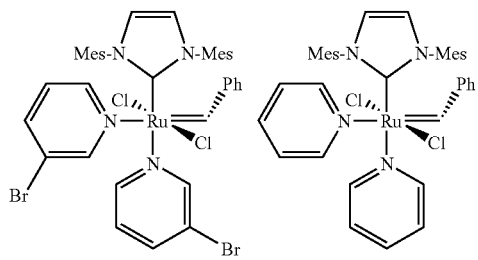
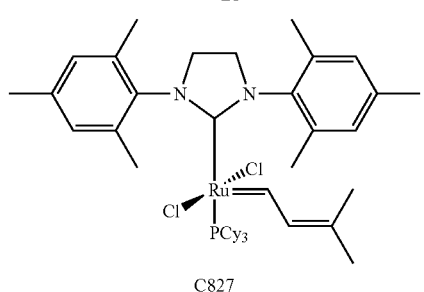
C827

29
-continued
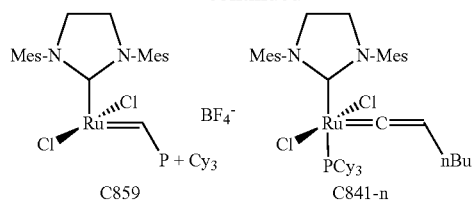
C859    C841-n
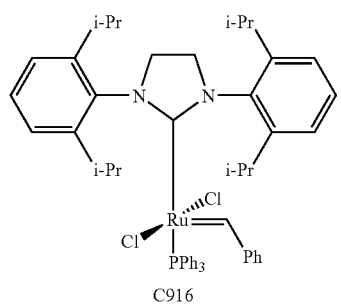
C916
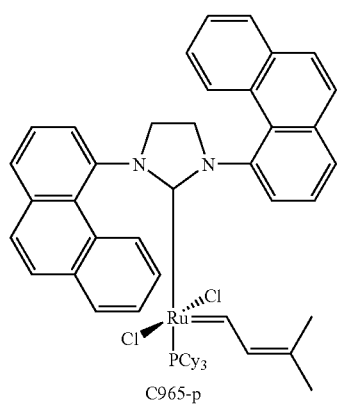
C965-p
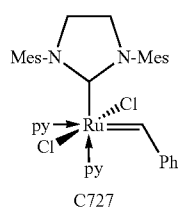
C727
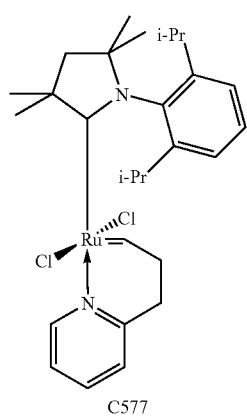
C577
30
-continued
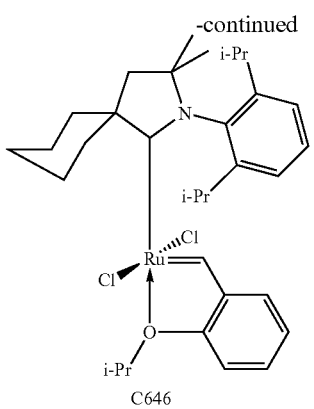
C646
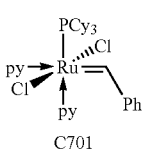
C701
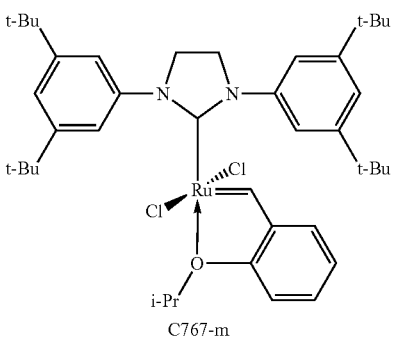
C767-m
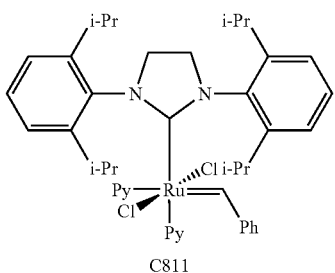
C811
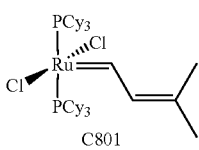
C801
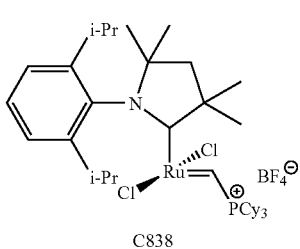
C838

-continued
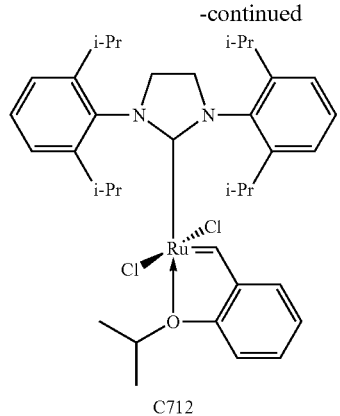
C712
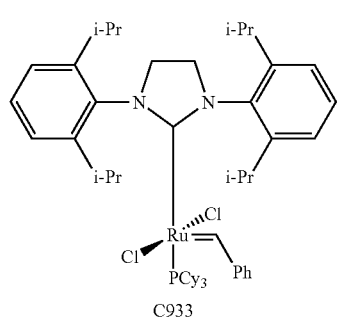
C933
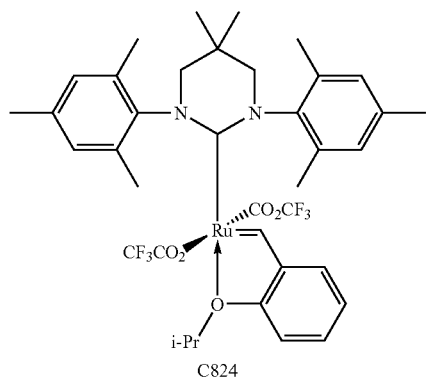
C824
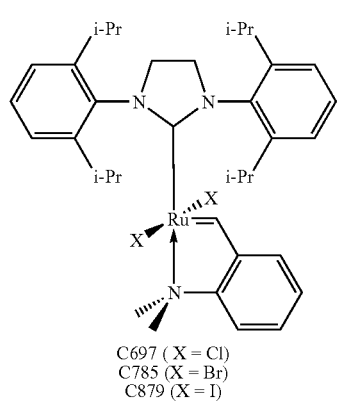
C697 (X = Cl)
C785 (X = Br)
C879 (X = I)
-continued
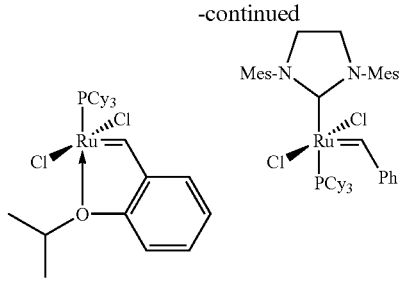
C601    C848
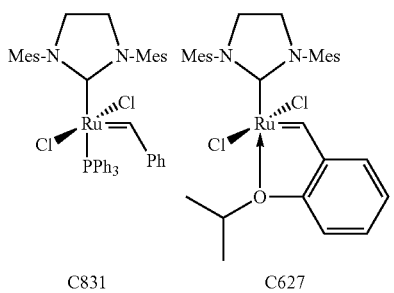
C831    C627
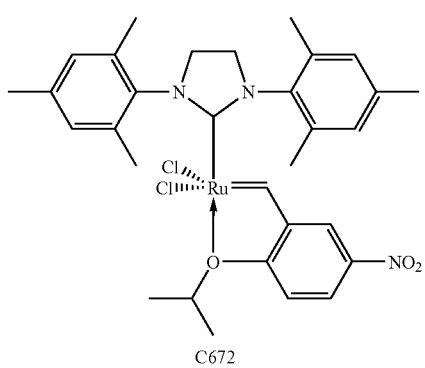
C672
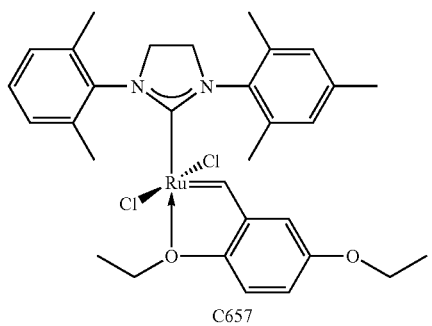
C657
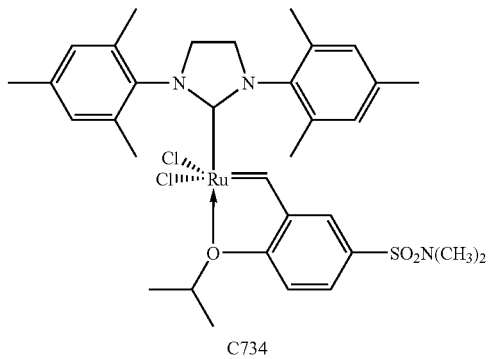
C734

-continued
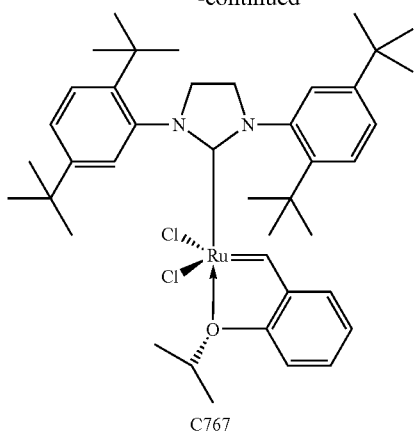
C767
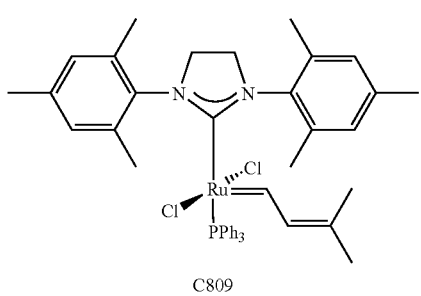
C809
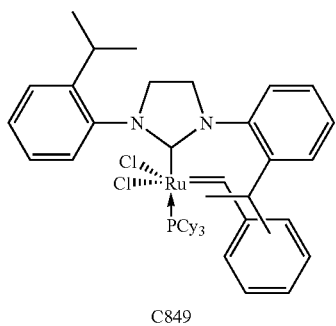
C849
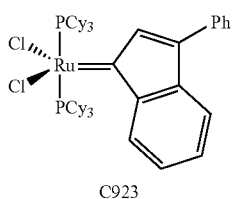
C923
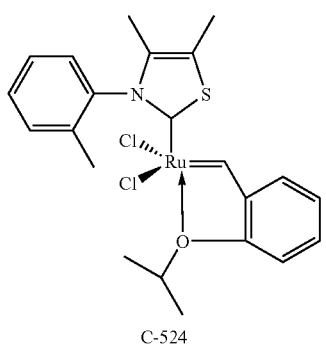
C-524
-continued
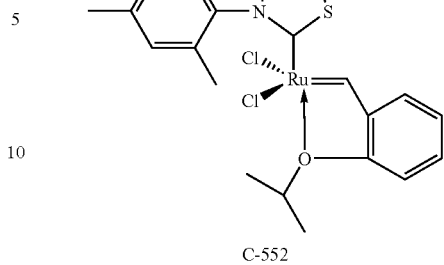
C-552
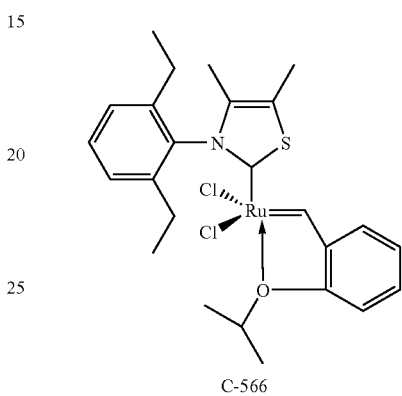
C-566
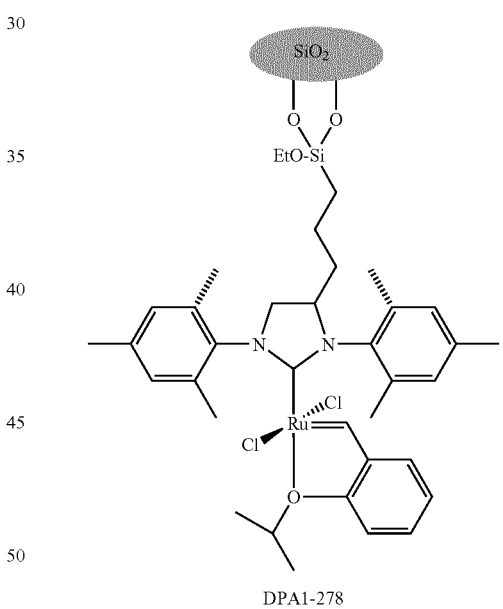
DPA1-278
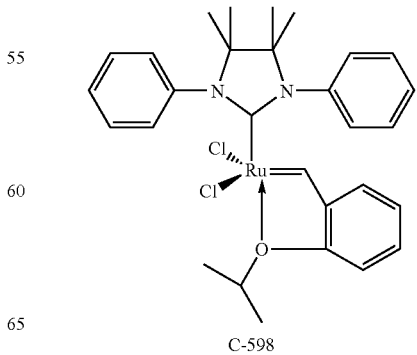
C-598

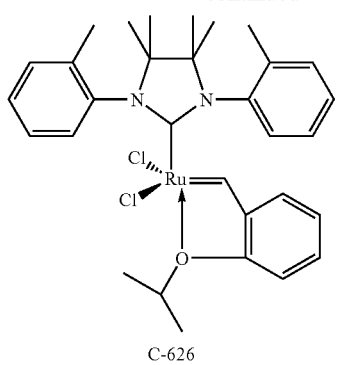
C-626
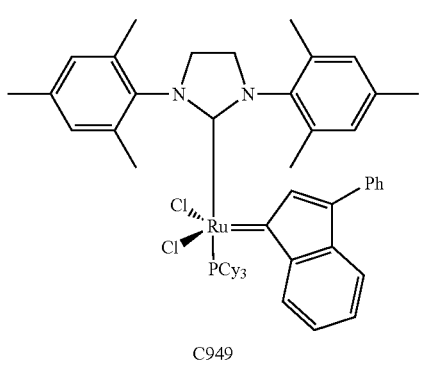
C949
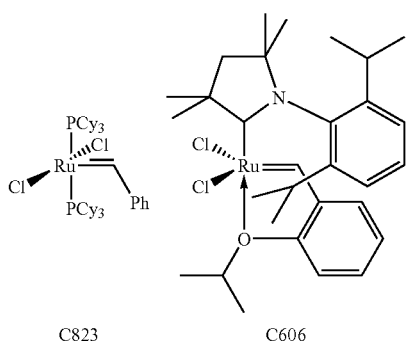
C823  C606
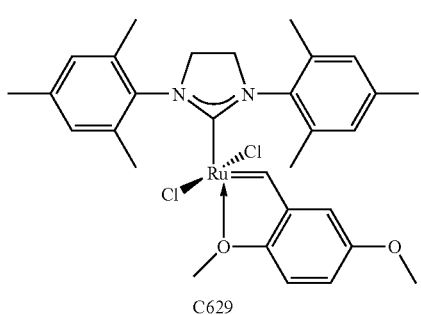
C629
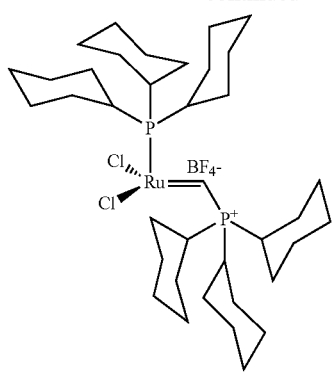
C833
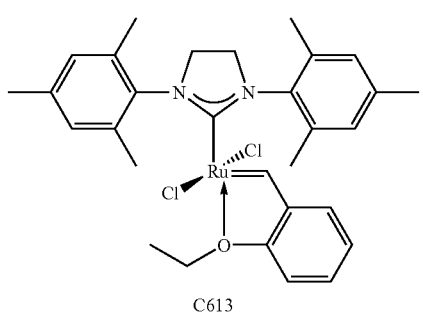
C613
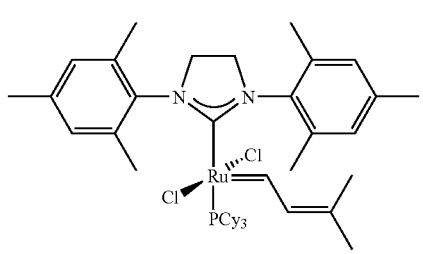
C827
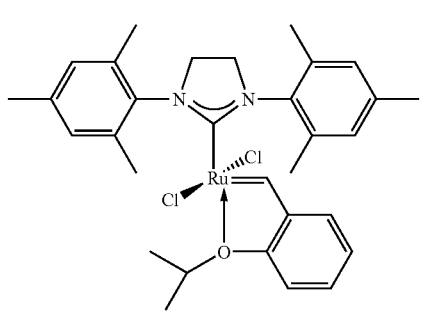
C627
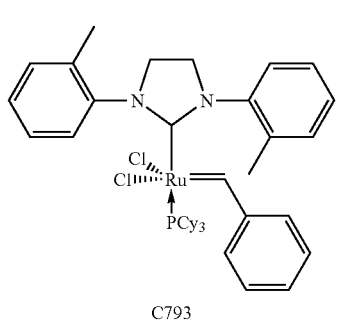
C793

-continued

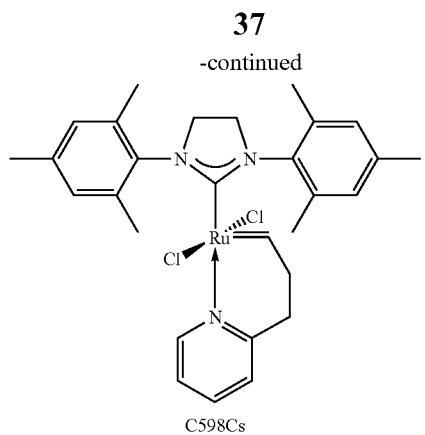
C598Cs

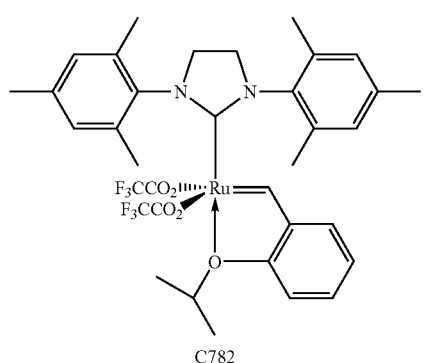
C782

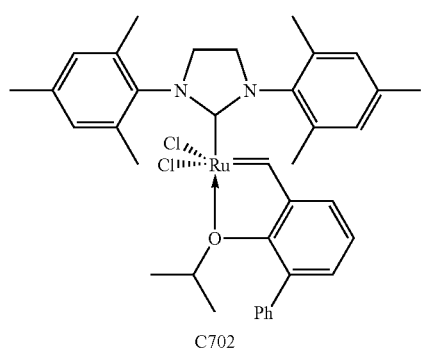
C702

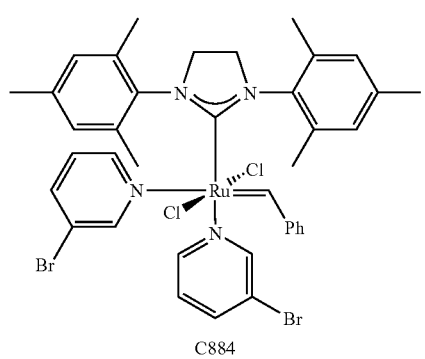
C884

-continued

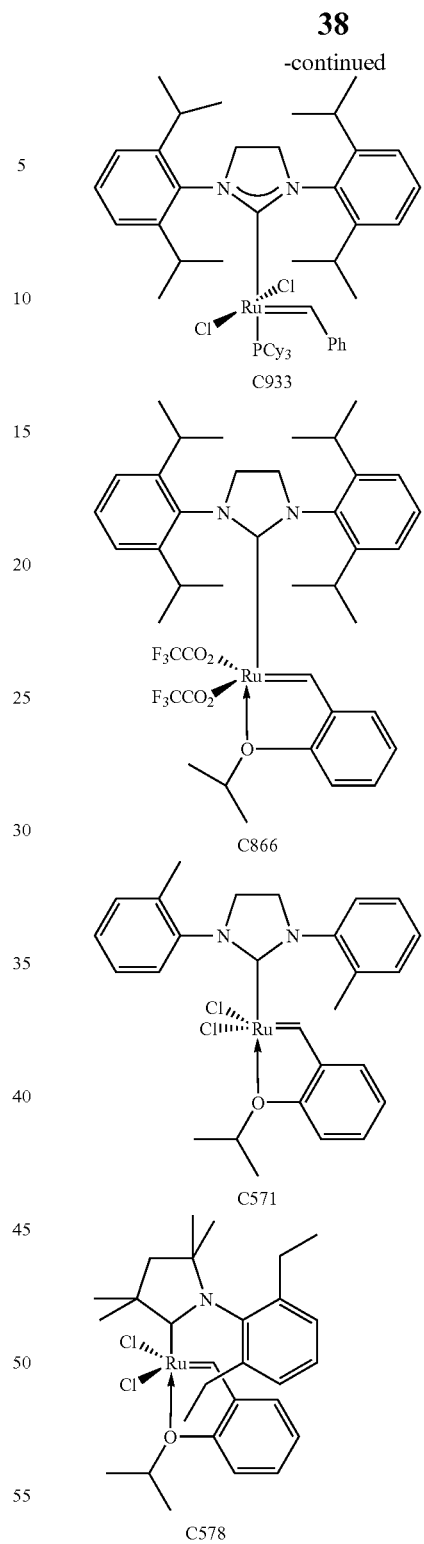

In the foregoing molecular structures and formulae, Ph represents phenyl, Cy represents cyclohexane, Me represents methyl, nBu represents n-butyl, i-Pr represents isopropyl, py represents pyridine (coordinated through the N atom), and Mes represents mesityl (i.e., 2,4,6-trimethylphenyl).

Further examples of catalysts useful in the reactions of the present disclosure include the following: ruthenium (II) dichloro(3-methyl-1,2-butenylidene) bis(tricyclopentylphosphine) (C716); ruthenium (II) dichloro (3-methyl-1, 2-butenylidene) bis(tricyclohexylphosphine) (C801); ruthenium (II) dichloro (phenylmethylene) bis(tricyclohexylphosphine) (C823); ruthenium (II) [1,3-bis-(2,4,6-trimethylphenyl)-2-imidazolidinylidene] dichloro (phenylmethylene) (triphenylphosphine) (C830), and ruthenium (II) dichloro (vinyl phenylmethylene) bis(tricyclohexylphosphine) (C835); ruthenium (II) dichloro (tricyclohexylphosphine) (o-isopropoxyphenylmethylene) (C601), and ruthenium (II) (1,3-bis-(2, 4, 6,-trimethylphenyl)-2-imidazolidinylidene) dichloro (phenylmethylene) (bis 3-bromopyridine (C884)).

Exemplary ruthenium-based metathesis catalysts include those represented by structures 12 (commonly known as Grubbs's catalyst), 14 and 16. Structures 18, 20, 22, 24, 26, 28, 60, 62, 64, 66, and 68 represent additional ruthenium-based metathesis catalysts. Catalysts C627, C682, C697, C712, and C827 represent still additional ruthenium-based catalysts. General structures 50 and 52 represent additional ruthenium-based metathesis catalysts of the type reported in *Chemical & Engineering News*; Feb. 12, 2007, at pages 37-47. In the structures, Ph is phenyl, Mes is mesityl, py is pyridine, Cp is cyclopentyl, and Cy is cyclohexyl.

Techniques for using the metathesis catalysts are known in the art (see, for example, U.S. Pat. Nos. 7,102,047; 6,794,534; 6,696,597; 6,414,097; 6,306,988; 5,922,863; 5,750,815; and metathesis catalysts with ligands in U.S. Publication No. 2007/0004917 A1), all incorporated by reference herein in their entireties. A number of the metathesis catalysts as shown are manufactured by Materia, Inc. (Pasadena, Calif.).

Additional exemplary metathesis catalysts include, without limitation, metal carbene complexes selected from the group consisting of molybdenum, osmium, chromium, rhenium, and tungsten. The term "complex" refers to a metal atom, such as a transition metal atom, with at least one ligand or complexing agent coordinated or bound thereto. Such a ligand typically is a Lewis base in metal carbene complexes useful for alkyne or alkene-metathesis. Typical examples of such ligands include phosphines, halides and stabilized carbenes. Some metathesis catalysts may employ plural metals or metal co-catalysts (e.g., a catalyst comprising a tungsten halide, a tetraalkyl tin compound, and an organoaluminum compound).

An immobilized catalyst can be used for the metathesis process. An immobilized catalyst is a system comprising a catalyst and a support, the catalyst associated with the support. Exemplary associations between the catalyst and the support may occur by way of chemical bonds or weak interactions (e.g. hydrogen bonds, donor acceptor interactions) between the catalyst, or any portions thereof, and the support or any portions thereof. Support is intended to include any material suitable to support the catalyst. Typically, immobilized catalysts are solid phase catalysts that act on liquid or gas phase reactants and products. Exemplary supports are polymers, silica or alumina. Such an immobilized catalyst may be used in a flow process. An immobilized catalyst can simplify purification of products and recovery of the catalyst so that recycling the catalyst may be more convenient.

The metathesis process can be conducted under any conditions adequate to produce the desired metathesis products. For example, stoichiometry, atmosphere, solvent, temperature and pressure can be selected to produce a desired product and to minimize undesirable byproducts. The metathesis process may be conducted under an inert atmosphere. Similarly, if a reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen and combinations thereof.

Similarly, if a solvent is used, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc.

In certain embodiments, a ligand may be added to the metathesis reaction mixture. In many embodiments using a ligand, the ligand is selected to be a molecule that stabilizes the catalyst, and may thus provide an increased turnover number for the catalyst. In some cases the ligand can alter reaction selectivity and product distribution. Examples of ligands that can be used include Lewis base ligands, such as, without limitation, trialkylphosphines, for example tricyclohexylphosphine and tributyl phosphine; triarylphosphines, such as triphenylphosphine; diarylalkylphosphines, such as, diphenylcyclohexylphosphine; pyridines, such as 2,6-dimethylpyridine, 2,4,6-trimethylpyridine; as well as other Lewis basic ligands, such as phosphine oxides and phosphinites. Additives may also be present during metathesis that increase catalyst lifetime.

Any useful amount of the selected metathesis catalyst can be used in the process. For example, the molar ratio of the unsaturated polyol ester to catalyst may range from about 5:1 to about 10,000,000:1 or from about 50:1 to 500,000:1.

The metathesis reaction temperature may be a rate-controlling variable where the temperature is selected to provide a desired product at an acceptable rate. The metathesis temperature may be greater than $-40°$ C., may be greater than about $-20°$ C., and is typically greater than about $0°$ C. or greater than about $20°$ C. Typically, the metathesis reaction temperature is less than about $150°$ C., typically less than about $120°$ C. An exemplary temperature range for the metathesis reaction ranges from about $20°$ C. to about $120°$ C.

The metathesis reaction can be run under any desired pressure. Typically, it will be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than about 10 kPa, in some embodiments greater than about 30 kP, or greater than about 100 kPa. Typically, the reaction pressure is no more than about 7000 kPa, in some embodiments no more than about 3000 kPa. An exemplary pressure range for the metathesis reaction is from about 100 kPa to about 3000 kPa.

In some embodiments, the metathesis reaction is catalyzed by a system containing both a transition and a non-transition metal component. The most active and largest number of catalyst systems are derived from Group VI A transition metals, for example, tungsten and molybdenum.

Separation Step (Step (c)):

After cross-metathesis with the short-chain olefin, at least a portion of the acid-, ester-, or salt-functionalized alkene is separated from the remaining cross-metathesis products. Useful techniques for separating the acid-, ester-, or salt-functionalized alkene include, for example, distillation, reactive distillation, chromatography, fractional crystallization, membrane separation, liquid/liquid extraction, or a combination thereof.

Catalytic Modification (Step (d)):

According to the method of the invention, after separation, the carbon-carbon double bond of the separated acid-, ester-, or carboxylate salt-functionalized alkene is catalytically modified by hydrocyanation in order to introduce a nitrile group into the molecule. In some embodiments, the nitrile group is then further reacted to form an amine group, a carboxylic acid group, an aldehyde group, or an alcohol group.

Hydrocyanation is a catalytic process where hydrogen cyanide is added to an alkene having n carbon atoms, to produce a nitrile having n+1 carbon atoms, with n≥1. In many embodiments, prior to hydrocyanation, the internal functionalized alkene is isomerized to form a terminal functionalized alkene. Isomerization and hydrocyanation of an exemplary acid-, ester-, or salt-functionalized compound is shown below:

R'OOC—(CH$_2$)$_n$—CH=CH—CH$_3$ ↔ R'OOC—(CH$_2$)$_n$—CH$_2$—CH=CH$_2$, R'OOC—(CH$_2$)$_n$—CH$_2$—CH=CH$_2$+HCN/catalyst→R'OOC—(CH$_2$)$_n$—CH$_2$—CH(—C≡N)—CH$_3$+R'OOC—(CH$_2$)$_n$—CH$_2$—CH$_2$—CH$_2$—C≡N where —R' is hydrogen (acid), an aliphatic group (ester), or a metal ion (salt).

As shown above, hydrocyanation may result in the formation of branched or linear species depending upon the location of the carbon-carbon double bond and whether isomerization of the double bond occurs before the hydrocyanation reaction. Typical hydrocyanation catalysts include low valent nickel phosphite catalysts. Optionally, the nitrile group may be hydrogenated to convert it into a primary amine group as shown below:

R'OOC—(CH$_2$)$_n$—CH$_2$—CH(C≡N)—CH$_3$+H$_2$/catalyst→R'OOC—(CH$_2$)$_n$—CH$_2$—CH(—CH$_2$—NH$_2$)—CH$_3$ R'OOC—(CH$_2$)$_n$—CH$_2$—CH$_2$—CH$_2$—C≡N+H$_2$/catalyst→R'OOC—(CH$_2$)$_n$—CH$_2$—CH$_2$—CH$_2$—CH$_2$—NH$_2$ where —R' is hydrogen (acid), an aliphatic group (ester), or a metal ion (salt). Examples of hydrogenation catalysts include Ru, Pt, Pd, Rh, and Re catalysts.

The method of the invention can be employed to synthesize various organic compounds. The organic compounds produced in accordance with the method of the present invention will depend upon the starting composition that is chosen and the catalytic modification. For example, an ester-functionalized starting composition can be catalytically modified using hydrocyanation to produce an ester-nitrile compound. In similar fashion, an acid-functionalized starting composition can be catalytically modified by hydrocyanation to produce an organic compound having carboxylic acid functionality and nitrile functionality. The nitrile group may also be modified to an aldehyde, alcohol, carboxylic acid, or amine group. Additional examples are summarized in TABLE C.

TABLE C

| Functionality of Starting Composition | Catalytic Modification | Functionality of Product Organic Compound |
|---|---|---|
| Acid | Hydrocyanation & Hydrogenation | Acid - Amine |
| Acid | Hydrocyanation & Hydrolysis | Diacid |
| Acid | Hydrocyanation & Reduction | Acid - Aldehyde |
| Acid | Hydrocyanation & Reduction | Acid - Alcohol |
| Ester | Hydrocyanation & Hydrogenation | Ester - Amine |
| Ester | Hydrocyanation & Hydrolysis | Ester - Acid |
| Ester | Hydrocyanation & Reduction | Ester - Aldehyde |
| Ester | Hydrocyanation & Reduction | Ester - Alcohol |

The length of the product organic made in accordance with the method of the invention can be varied depending upon the starting composition that is chosen and the position of the carbon-carbon double bond in the starting composition. Typically, the organic compounds will have a chain length of about 8 to 16 carbon atoms. For example, when Δ9 starting compositions are used, the method of the invention produces organic compounds having a chain length of 12 carbon atoms (C12) when 3-hexene is used as the short chain alkene in the cross-metathesis reaction. A summary of the starting composition and the chain length of the resulting organic compound is provided in TABLE D.

TABLE D

| Starting Composition | Chain Length of Organic Compound |
|---|---|
| Δ4 | 7 |
| Δ5 | 8 |
| Δ6 | 9 |
| Δ8 | 11 |
| Δ9 | 12 |
| Δ11 | 14 |
| Δ13 | 16 |

Using the method of the invention it is possible to synthesize a large number of organic compounds having a variety of chain lengths and functional groups. A summary of some organic compounds that can be synthesized using the method of the invention is provided in TABLE E.

TABLE E

| Starting Composition | Cross-Metathesis Reagent | Functionalized Alkene Intermediate | Catalytic Modification | Products |
|---|---|---|---|---|
| Δ9 methyl ester | 2-butene | Methyl ester of 9-undecenoic acid | Hydrocyanation & Hydrogenation | Methyl 12-aminododecanoate H$_2$N(CH$_2$)$_{11}$CO$_2$CH$_3$ |
| Δ9 methyl ester | 2-butene | Methyl ester of 9-undecenoic acid | Hydrocyanation & Hydrolysis | Methyl 11-carboxyundecanoate HOOC(CH$_2$)$_{10}$CO$_2$CH$_3$ |
| Δ9 methyl ester | 2-butene | Methyl ester of 9-undecenoic acid | Hydrocyanation & Reduction | Methyl 12-oxododecanoate OHC(CH$_2$)$_{10}$CO$_2$CH$_3$ |

TABLE E-continued

| Starting Composition | Cross-Metathesis Reagent | Functionalized Alkene Intermediate | Catalytic Modification | Products |
|---|---|---|---|---|
| Δ9 methyl ester | 2-butene | Methyl ester of 9-undecenoic acid | Hydrocyanation & Reduction | Methyl 12-hydroxydodecanoate $HO(CH_2)_{11}CO_2CH_3$ |
| Δ9 acid | 2-butene | 9-undecenoic acid | Hydrocyanation & Hydrogenation | 12-Aminododecanoic acid $H_2N(CH_2)_{11}CO_2H$ |
| Δ9 acid | 2-butene | 9-undecenoic acid | Hydrocyanation & Hydrolysis | 1,12-Dodecanedioc acid $HOOC(CH_2)_{10}COOH$ |
| Δ9 acid | 2-butene | 9-undecenoic acid | Hydrocyanation & Reduction | 12-oxododecanoic acid $OHC(CH_2)_{10}CO_2H$ |
| Δ9 acid | 2-butene | 9-undecenoic acid | Hydrocyanation & Reduction | 12-Hydroxydodecanoic acid $HO(CH_2)_{11}CO_2H$ |

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims. All patents, patent documents, and publications cited herein are hereby incorporated by reference as if individually incorporated.

What is claimed is:

1. A method of making an organic compound, the method comprising:
   (a) providing a starting composition comprising an unsaturated glyceride represented by the formula:

$CH_2A$-$CHB$—$CH_2C$ wherein -A, —B, and —C are independently selected from the group consisting of:
   —OH;
   —O(O)C—$(CH_2)_{n2}$-[—CH=CH—$(CH_2)_{n3}$-$]_x$—$(CH_2)_{n1}$—$CH_3$; and
   —O(O)C—R';
   with the proviso that at least one of -A, —B, or —C is
   —O(O)C—$(CH_2)_{n2}$—[—CH=CH—$(CH_2)_{n3}$-$]_x$—$(CH_2)_{n1}$—$CH_3$
   and wherein
   R' is a straight or branched chain alkyl or alkenyl group;
   n1 is an integer equal to or greater than 0;
   n2 is an integer equal to or greater than 0;
   n3 is an integer equal to or greater than 0; and
   x is an integer equal to or greater than 1;
   (b) cross-metathesizing the unsaturated glyceride with a short-chain olefin in the presence of a metathesis catalyst to form cross-metathesis products comprising:
      (i) one or more olefin compounds; and
      (ii) one or more metathesized unsaturated glycerides, wherein the short-chain olefin is an α-olefin selected from the group consisting of 1-butene, 1-pentene, 1-hexene, 1-heptene, 1-octene, 1-nonene, and combinations thereof;
   (c) separating at least a portion of the one or more metathesized unsaturated glycerides from the cross-metathesis products;
   (d) isomerizing the separated one or more metathesized unsaturated glycerides to form one or more isomerized separated metathesized unsaturated glycerides having a terminal olefin; and
   (e) catalytically modifying the carbon-carbon double bond of the one or more separated metathesized unsaturated glycerides or the one or more isomerized separated metathesized unsaturated glycerides by hydrocyanation to form a hydrocyanated glyceride.

2. The method of claim 1, further comprising one of the steps of (i) reducing the nitrile group of the hydrocyanated glyceride to form an aldehyde group or an alcohol group, (ii) hydrolyzing the nitrile group of the hydrocyanated glyceride to form a carboxylic acid group, or (iii) hydrogenating the nitrile group of the hydrocyanated glyceride to form an amine group.

3. The method of claim 1, wherein the starting composition is selected from the group consisting of: soybean oil, rapeseed oil, corn oil, sesame oil, cottonseed oil, sunflower oil, canola oil, safflower oil, palm oil, palm kernel oil, linseed oil, castor oil, olive oil, peanut oil, algae oil, tall oil, fish oil, lard, tallow, and combinations thereof.

4. The method of claim 1, wherein the metathesis catalyst is a ruthenium alkylidene metathesis catalyst.

5. The method of claim 1, wherein:
   n1 is an integer from 0 to 15;
   n2 is an integer from 2 to 11;
   n3 is an integer from 0 to 6; and
   x is an integer from 1 to 6.

6. The method of claim 5, wherein n2 is 7.

7. The method of claim 6, wherein x is 1, n1 is 6, and n3 is 1.

8. The method of claim 6, wherein x is 2, n1 is 3, and n3 is 1.

9. The method of claim 6, wherein x is 3, n1 is 0, and n3 is 1.

* * * * *